US010689646B2

(12) United States Patent
De Kimpe et al.

(10) Patent No.: US 10,689,646 B2
(45) Date of Patent: Jun. 23, 2020

(54) TREATMENT OF GENETIC DISORDERS ASSOCIATED WITH DNA REPEAT INSTABILITY

(71) Applicant: BioMarin Technologies B.V., Leiden (NL)

(72) Inventors: Josephus Johannes De Kimpe, Utrecht (NL); Gerard Johannes Platenburg, Voorschoten (NL); Derick Gert Wansink, Arnhem (NL)

(73) Assignee: BioMarin Technologies B.V. (NL)

( * ) Notice: Subject to any disclaimer, the term of this patent is extended or adjusted under 35 U.S.C. 154(b) by 0 days.

(21) Appl. No.: 15/855,848

(22) Filed: Dec. 27, 2017

(65) Prior Publication Data

US 2018/0112214 A1    Apr. 26, 2018

Related U.S. Application Data

(62) Division of application No. 14/809,483, filed on Jul. 27, 2015, now Pat. No. 9,890,379, which is a division of application No. 12/377,160, filed as application No. PCT/NL2007/050399 on Aug. 10, 2007, now abandoned.

(30) Foreign Application Priority Data

Aug. 11, 2006  (EP) .................................... 06118809
Aug. 21, 2006  (EP) .................................... 06119247

(51) Int. Cl.
| | | |
|---|---|---|
| *C12N 15/113* | (2010.01) | |
| *C12N 15/11* | (2006.01) | |
| *C12Q 1/6883* | (2018.01) | |
| *A61K 48/00* | (2006.01) | |

(52) U.S. Cl.
CPC ............ *C12N 15/11* (2013.01); *C12N 15/113* (2013.01); *C12Q 1/6883* (2013.01); *A61K 48/00* (2013.01); *C12N 2310/11* (2013.01); *C12N 2310/315* (2013.01); *C12N 2310/321* (2013.01); *C12N 2310/346* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 5,418,139 A | 5/1995 | Campbell |
| 5,541,308 A | 7/1996 | Hogan et al. |
| 5,593,974 A | 1/1997 | Rosenberg et al. |
| 5,608,046 A | 3/1997 | Cook et al. |
| 5,627,263 A | 5/1997 | Ruoslahti et al. |
| 5,658,764 A | 8/1997 | Pergolizzi et al. |
| 5,741,645 A | 4/1998 | Orr et al. |
| 5,766,847 A | 6/1998 | Jaeckle et al. |
| 5,853,995 A | 12/1998 | Lee |
| 5,869,252 A | 2/1999 | Bouma et al. |
| 5,916,808 A | 6/1999 | Kole et al. |
| 5,945,290 A | 8/1999 | Cowsert |
| 5,962,332 A | 10/1999 | Singer et al. |
| 5,968,909 A | 10/1999 | Agrawal et al. |
| 5,976,879 A | 11/1999 | Kole et al. |
| 6,124,100 A | 9/2000 | Jin |
| 6,130,207 A | 10/2000 | Dean et al. |
| 6,133,031 A | 10/2000 | Monia et al. |
| 6,172,208 B1 | 1/2001 | Cook |
| 6,172,216 B1 | 1/2001 | Bennett et al. |
| 6,210,892 B1 | 4/2001 | Bennett et al. |
| 6,251,589 B1 | 6/2001 | Tsuji et al. |
| 6,280,938 B1 | 8/2001 | Ranum et al. |
| 6,300,060 B1 | 10/2001 | Kantoff et al. |
| 6,322,978 B1 | 11/2001 | Kahn et al. |
| 6,329,501 B1 | 12/2001 | Smith et al. |
| 6,355,481 B1 | 3/2002 | Li et al. |
| 6,355,690 B1 | 3/2002 | Tsuji |
| 6,369,038 B1 | 4/2002 | Blumenfeld et al. |
| 6,379,698 B1 | 4/2002 | Leamon |
| 6,399,575 B1 | 6/2002 | Smith et al. |
| 6,514,755 B1 | 2/2003 | Ranum et al. |
| 6,623,927 B1 | 9/2003 | Brahmachari et al. |

(Continued)

FOREIGN PATENT DOCUMENTS

| | | |
|---|---|---|
| CA | 2319149 A1 | 10/2001 |
| CA | 2526893 A1 | 11/2004 |

(Continued)

OTHER PUBLICATIONS

Aartsma-Rus et al., "Antisense-Induced Multiexon Skipping for Duchenne Muscular Dystrophy Makes More Sense," American Journal of Human Genetics, vol. 74, pp. 83-92, 2004.
Aartsma-Rus et al., "Comparative Analysis of Antisense Oligonucleotide Analogs for Targeted DMD Exon 46 Skipping in Muscle Cells," Gene Therapy, vol. 11 (18), pp. 1391-1398, 2004.
Aartsma-Rus, A., et al., "Antisense Mediated Exon Skipping; A Versatile Tool with Therapeutic and Research Applications," RNA, vol. 13 (10), pp. 1609-1624, 2007.
Aartsma-Rus, A., et al., "Antisense-Induced Exon Skipping for Duplications in Duchenne Muscular Dystrophy," BMC Medical Genetics, vol. 8 (43), 9 pages, 2007.

(Continued)

*Primary Examiner* — J. E. Angell
(74) *Attorney, Agent, or Firm* — Lathrop GPM LLP; James H. Velema, Esq.

(57) ABSTRACT

The current invention provides for methods and medicaments that apply oligonucleotide molecules complementary only to a repetitive sequence in a human gene transcript, for the manufacture of a medicament for the diagnosis, treatment or prevention of a cis-element repeat instability associated genetic disorders in humans. The invention hence provides a method of treatment for cis-element repeat instability associated genetic disorders. The invention also pertains to modified oligonucleotides which can be applied in method of the invention to prevent the accumulation and/or translation of repeat expanded transcripts in cells.

Figure 1:
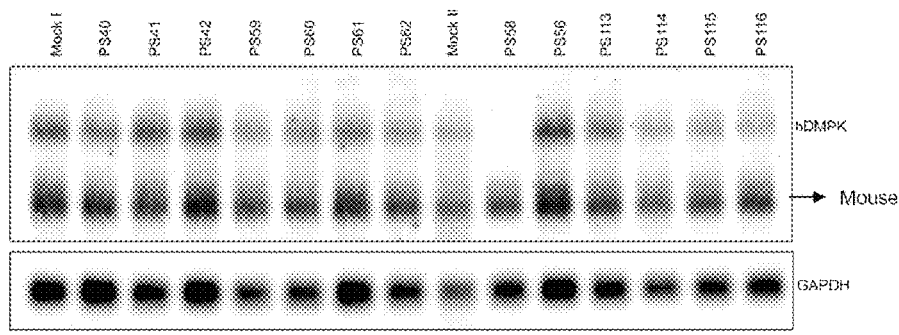

16 Claims, 5 Drawing Sheets
Specification includes a Sequence Listing.

(56) References Cited

U.S. PATENT DOCUMENTS

| | | |
|---|---|---|
| 6,653,466 B2 | 11/2003 | Matsuo |
| 6,653,467 B1 | 11/2003 | Matsuo et al. |
| 6,670,461 B1 | 12/2003 | Wengel et al. |
| 6,727,355 B2 | 4/2004 | Matsuo et al. |
| 6,794,192 B2 | 9/2004 | Parums et al. |
| 6,902,896 B2 | 6/2005 | Ranum et al. |
| 6,982,150 B2 | 1/2006 | Sheetz et al. |
| 7,001,994 B2 | 2/2006 | Zhu |
| 7,118,893 B2 | 10/2006 | Ranum et al. |
| 7,189,530 B2 | 3/2007 | Botstein et al. |
| 7,202,210 B2 | 4/2007 | Wolfman et al. |
| 7,250,404 B2 | 7/2007 | Felgner et al. |
| 7,355,018 B2 | 4/2008 | Glass |
| 7,405,193 B2 | 7/2008 | Lodish et al. |
| 7,442,782 B2 | 10/2008 | Ranum et al. |
| 7,514,551 B2 | 4/2009 | Rabbani et al. |
| 7,534,879 B2 | 5/2009 | Van Deutekom |
| 7,589,189 B2 | 9/2009 | Ichiro et al. |
| 7,655,785 B1 | 2/2010 | Bentwich |
| 7,771,727 B2 | 8/2010 | Fuselier et al. |
| 7,807,816 B2 | 10/2010 | Wilson et al. |
| 7,902,160 B2 | 3/2011 | Matsuo et al. |
| 7,960,541 B2 | 6/2011 | Wilton et al. |
| 7,973,015 B2 | 7/2011 | Van Ommen et al. |
| 8,232,384 B2 | 7/2012 | Wilton et al. |
| 8,263,760 B2 | 9/2012 | De Kimpe et al. |
| 8,268,962 B2 | 9/2012 | Heemskerk et al. |
| 8,304,398 B2 | 11/2012 | 't Hoen et al. |
| 8,361,979 B2 | 1/2013 | Aartsma-Rus et al. |
| 8,519,097 B2 | 8/2013 | Heemskerk et al. |
| 8,609,065 B2 | 12/2013 | Kuik-Romeijn et al. |
| 8,759,507 B2 | 6/2014 | Van Deutekom |
| 8,802,645 B2 | 8/2014 | Van Ommen |
| 9,057,066 B2 | 6/2015 | Hung et al. |
| 9,139,828 B2 | 9/2015 | Platenburg et al. |
| 9,243,245 B2 | 1/2016 | De Kimpe et al. |
| 9,499,818 B2 | 11/2016 | Van Deutekom et al. |
| 9,528,109 B2 | 12/2016 | De Kimpe et al. |
| 9,745,576 B2 | 8/2017 | De Visser et al. |
| 9,890,379 B2 | 2/2018 | De Kimpe et al. |
| 9,896,687 B2 | 2/2018 | Van Ommen et al. |
| 2001/0056077 A1 | 12/2001 | Matsuo |
| 2002/0049173 A1 | 4/2002 | Bennett et al. |
| 2002/0055481 A1 | 5/2002 | Matsuo et al. |
| 2002/0115824 A1 | 8/2002 | Engler et al. |
| 2002/0165150 A1 | 11/2002 | Ben-Sasson |
| 2003/0073215 A1 | 4/2003 | Baker et al. |
| 2003/0082763 A1 | 5/2003 | Baker et al. |
| 2003/0082766 A1 | 5/2003 | Baker et al. |
| 2003/0109476 A1 | 6/2003 | Kmiec et al. |
| 2003/0124523 A1 | 7/2003 | Asselbergs et al. |
| 2003/0134790 A1 | 7/2003 | Langenfeld |
| 2003/0235845 A1 | 12/2003 | Van Ommen et al. |
| 2003/0236214 A1 | 12/2003 | Wolff et al. |
| 2004/0101852 A1 | 5/2004 | Bennett et al. |
| 2004/0132684 A1 | 7/2004 | Sampath et al. |
| 2004/0226056 A1 | 11/2004 | Roch et al. |
| 2005/0096284 A1 | 5/2005 | McSwiggen |
| 2005/0222009 A1 | 10/2005 | Lamensdorf et al. |
| 2005/0246794 A1 | 11/2005 | Khvorova et al. |
| 2005/0277133 A1 | 12/2005 | McSwiggen |
| 2006/0074034 A1 | 4/2006 | Collins et al. |
| 2006/0099616 A1 | 5/2006 | Van Ommen et al. |
| 2006/0147952 A1 | 7/2006 | Van Ommen et al. |
| 2006/0148740 A1 | 7/2006 | Platenburg |
| 2007/0082861 A1 | 4/2007 | Matsuo et al. |
| 2007/0141628 A1 | 6/2007 | Cunningham et al. |
| 2007/0275914 A1 | 11/2007 | Manoharan et al. |
| 2007/0292408 A1 | 12/2007 | Singh et al. |
| 2007/0299027 A1 | 12/2007 | Hung et al. |
| 2008/0015158 A1 | 1/2008 | Ichiro et al. |
| 2008/0039418 A1 | 2/2008 | Freier |
| 2008/0207538 A1 | 8/2008 | Lawrence et al. |
| 2008/0209581 A1 | 8/2008 | Van Ommen et al. |
| 2008/0249294 A1 | 10/2008 | Haeberli et al. |
| 2009/0228998 A1 | 9/2009 | Van Ommen et al. |
| 2009/0312532 A1 | 12/2009 | Van Deutekom et al. |
| 2010/0081627 A1 | 4/2010 | Sampath et al. |
| 2010/0099750 A1 | 4/2010 | McSwiggen et al. |
| 2010/0184833 A1 | 7/2010 | De Kimpe et al. |
| 2011/0015258 A1 | 1/2011 | Wilton et al. |
| 2011/0184050 A1 | 7/2011 | De Kimpe et al. |
| 2011/0263682 A1 | 10/2011 | De Kimpe et al. |
| 2012/0022134 A1 | 1/2012 | De Kimpe et al. |
| 2012/0029057 A1 | 2/2012 | Wilton et al. |
| 2012/0029058 A1 | 2/2012 | Wilton et al. |
| 2012/0041050 A1 | 2/2012 | Wilton et al. |
| 2012/0046342 A1 | 2/2012 | Van Deutekom et al. |
| 2012/0122801 A1 | 5/2012 | Platenburg |
| 2013/0072671 A1 | 3/2013 | Van Deutekom et al. |
| 2013/0302806 A1 | 11/2013 | Van Deutekom |
| 2014/0045763 A1 | 2/2014 | Aguilera et al. |
| 2014/0113955 A1 | 4/2014 | De Kimpe et al. |
| 2014/0128592 A1 | 5/2014 | De Kimpe et al. |
| 2014/0213635 A1 | 7/2014 | Van Deutekom |
| 2014/0221458 A1 | 8/2014 | De Kimpe et al. |
| 2014/0275212 A1 | 9/2014 | Van Deutekom |
| 2014/0350076 A1 | 11/2014 | Van Deutekom |
| 2014/0357698 A1 | 12/2014 | Van Deutekom et al. |
| 2014/0357855 A1 | 12/2014 | Van Deutekom et al. |
| 2014/0378527 A1 | 12/2014 | Van Deutekom |
| 2015/0045413 A1 | 2/2015 | De Visser et al. |
| 2015/0080563 A2 | 3/2015 | Van Deutekom et al. |
| 2015/0148404 A1 | 5/2015 | De Visser et al. |
| 2015/0191725 A1 | 7/2015 | Van Deutekom |
| 2015/0203849 A1 | 7/2015 | Van Deutekom et al. |
| 2015/0218559 A1 | 8/2015 | Van Deutekom et al. |
| 2015/0322434 A1 | 11/2015 | Van Deutekom |
| 2015/0361424 A1 | 12/2015 | Van Deutekom |
| 2016/0053262 A1 | 2/2016 | Platenburg et al. |
| 2016/0168570 A1 | 6/2016 | Van Deutekom et al. |
| 2016/0194636 A1 | 7/2016 | Van Deutekom et al. |
| 2016/0251658 A1 | 9/2016 | Van Deutekom et al. |
| 2016/0264967 A1 | 9/2016 | Van Deutekom et al. |
| 2016/0304864 A1 | 10/2016 | De Kimpe et al. |
| 2016/0355810 A1 | 12/2016 | Van Deutekom |
| 2017/0029818 A1 | 2/2017 | De Visser et al. |
| 2017/0029820 A1 | 2/2017 | Aguilera et al. |
| 2017/0044534 A1 | 2/2017 | Van Deutekom |
| 2017/0107512 A1 | 4/2017 | De Kimpe et al. |

FOREIGN PATENT DOCUMENTS

| | | |
|---|---|---|
| CN | 101501193 A | 8/2009 |
| CN | 101980726 A | 2/2011 |
| EP | 0558697 A1 | 9/1993 |
| EP | 0614977 A2 | 9/1994 |
| EP | 0438512 B1 | 12/1997 |
| EP | 0850300 A1 | 7/1998 |
| EP | 1015628 A1 | 7/2000 |
| EP | 1054058 A1 | 11/2000 |
| EP | 1133993 A1 | 9/2001 |
| EP | 1160318 A2 | 12/2001 |
| EP | 1191097 A1 | 3/2002 |
| EP | 1191098 A2 | 3/2002 |
| EP | 1380644 A1 | 1/2004 |
| EP | 1487493 A2 | 12/2004 |
| EP | 1495769 A1 | 1/2005 |
| EP | 1501931 A2 | 2/2005 |
| EP | 1544297 A2 | 6/2005 |
| EP | 1567667 A1 | 8/2005 |
| EP | 1568769 A1 | 8/2005 |
| EP | 1619249 A1 | 1/2006 |
| KR | 20030035047 A | 5/2003 |
| WO | WO 1993/001286 A2 | 1/1993 |
| WO | WO 1994/028175 A1 | 12/1994 |
| WO | WO 1995/016718 A1 | 6/1995 |
| WO | WO 1995/030774 A1 | 11/1995 |
| WO | WO 1997/012899 A1 | 4/1997 |
| WO | WO 1997/030067 A1 | 8/1997 |
| WO | WO 1998/018920 A1 | 5/1998 |
| WO | WO 1998/049345 A1 | 11/1998 |
| WO | WO 1998/053804 A1 | 12/1998 |
| WO | WO 2001/079283 A1 | 10/2001 |

(56) References Cited

FOREIGN PATENT DOCUMENTS

| | | |
|---|---|---|
| WO | WO 2001/083503 A2 | 11/2001 |
| WO | WO 2001/083695 A2 | 11/2001 |
| WO | WO 2002/002406 A1 | 1/2002 |
| WO | WO 2002/024906 A1 | 3/2002 |
| WO | WO 2002/026812 A1 | 4/2002 |
| WO | WO 2002/029056 A2 | 4/2002 |
| WO | WO 2003/002739 A1 | 1/2003 |
| WO | WO 2003/004511 A2 | 1/2003 |
| WO | WO 2003/013437 A2 | 2/2003 |
| WO | WO 2003/014145 A2 | 2/2003 |
| WO | WO 2003/037172 A2 | 5/2003 |
| WO | WO 2003/095647 A2 | 11/2003 |
| WO | WO 2004/011060 A2 | 2/2004 |
| WO | WO 2004/015106 A1 | 2/2004 |
| WO | WO 2004/016787 A1 | 2/2004 |
| WO | WO 2004/037854 A1 | 5/2004 |
| WO | WO 2004/048570 A1 | 6/2004 |
| WO | WO 2004/083432 A1 | 9/2004 |
| WO | WO 2004/101787 A1 | 11/2004 |
| WO | WO 2004/108157 A2 | 12/2004 |
| WO | WO 2005/019453 A2 | 3/2005 |
| WO | WO 2005/023836 A2 | 3/2005 |
| WO | WO 2005/035550 A2 | 4/2005 |
| WO | WO 2005/085476 A1 | 9/2005 |
| WO | WO 2005/086768 A2 | 9/2005 |
| WO | WO 2005/105995 A2 | 11/2005 |
| WO | WO 2005/115439 A2 | 12/2005 |
| WO | WO 2005/116204 A1 | 12/2005 |
| WO | WO 2006/000057 A1 | 1/2006 |
| WO | WO 2006/007910 A1 | 1/2006 |
| WO | WO 2006/017522 A2 | 2/2006 |
| WO | WO 2006/031267 A2 | 3/2006 |
| WO | WO 2006/054262 A2 | 5/2006 |
| WO | WO 2006/083800 A2 | 8/2006 |
| WO | WO 2007/044362 A2 | 4/2007 |
| WO | WO 2007/089584 A2 | 8/2007 |
| WO | WO 2009/008727 A2 | 1/2009 |
| WO | WO 2008/018795 A1 | 2/2009 |
| WO | WO 2009/099326 A2 | 8/2009 |
| WO | WO 2010/006237 A2 | 1/2010 |
| WO | WO 2010/014592 A1 | 2/2010 |
| WO | WO 2010/144485 A1 | 12/2010 |
| WO | WO 2011/097614 A1 | 8/2011 |
| WO | WO 2011/097641 A1 | 8/2011 |
| WO | WO 2012/012443 A2 | 1/2012 |
| WO | WO 2012/021985 A1 | 2/2012 |
| WO | WO 2012/109395 A1 | 8/2012 |
| WO | WO 2012/150960 A1 | 11/2012 |
| WO | WO 2013/082548 A1 | 6/2013 |
| WO | WO 2013/120003 A1 | 8/2013 |

OTHER PUBLICATIONS

Aartsma-Rus, A., et al., "Exploring The Frontiers of Therapeutic Exon Skipping for Duchenne Muscular Dystrophy by Double Targeting within One Or Multiple Exons," Molecular Therapy, vol. 14 (3), pp. 401-407, Sep. 2006.
Aartsma-Rus, A., et al., "Functional Analysis of 114 Exon-Internal AONs for Targeted DMD Exon Indication for Steric Hindrance of SR Protein Binding Sites," Oligonucleotides, vol. 15, pp. 284-297, 2005.
Aartsma-Rus, A., et al., "Guidelines for Antisense Oligonucleotide Design and Insight Into Splice-Modulating Mechanisms," Molecular Therapy, vol. 17 (3), pp. 548-553, Mar. 2009.
Aartsma-Rus, A., et al., "Targeted Exon Skipping as a Potential Gene Correction Therapy for Duchenne Muscular Dystrophy," Neuromuscular Disorders, vol. 12, pp. S71-S77, 2002.
Aartsma-Rus, A., et al., "Theoretic Applicability of Antisense-Mediated Exon Skipping for Duchenne Muscular Dystrophy Mutations," Human Mutation, vol. 30 (3), pp. 293-299, 2009.
Aartsma-Rus, A., et al., "Therapeutic Antisense-Induced Exon Skipping in Cultured Muscle Cells from Six Different DMD Patients," Human Molecular Genetics, vol. 12 (8), pp. 907-914, 2003.
Aartsma-Rus, A., et al., "Therapeutic Modulation of DMD Splicing by Blocking Exonic Splicing Enhancer Sites with Antisense Oligonucleotides," Annals of the New York Academy of Sciences, vol. 1082, pp. 74-76, 2006.
Abbs, S., et al., "A Convenient Multiplex PCR System for The Detection of Dystrophin Gene Deletions: A Comparative Analysis with cDNA Hybridisation Shows Mistypings by Both Methods," Journal of Medical Genetics, vol. 28, pp. 304-311, 1991.
Academisch Ziekenhuis Leiden, Request for an Opinion under Section 74(A) in relation to Patent No. EP (UK) 16192498, 33 pages, Apr. 20, 2009.
Agrawal, S., et al., "Antisense therapeutics: is it as simple as complementary base recognition?," Molecular Medicine Today, vol. 6, pp. 72-81, Feb. 2000.
Alter, J., et al., "Systemic delivery of morpholino oligonucleotide restores dystrophin expression bodywide and improves dystrophic pathology," Nature Medicine, 12(2), pp. 175-177, Feb. 2006.
Amalfitano, A., et al., "Dystrophin Gene, protein and cell biology: Structure and mutation of the dystrophin gene," Cambridge University Press, pp. 1-28, 1997.
Anderson, J., et al., "Correlated NOS-Iµ and myf5 expression by satellite cells in mdx mouse muscle regeneration during NOS manipulation and deflazacort treatment," Neuromuscular Disorders, vol. 13(5), pp. 388-396, Jun. 2003.
Anonymous, Third Party's Statement, Japanese Application No. 2002-529499, dated Oct. 29, 2010, 28 pages (English Translation attached).
Arap, W., et al., "Steps toward mapping the human vasculature by phage display," Nature Medicine, vol. 8, No. 2, pp. 121-127, Feb. 2002.
Arechavala-Gomeza, V., et al., "Comparative Analysis of Antisense Oligonucleotide Sequences for Targeted Skipping of Exon 51 During Dystrophin Pre-mRNA Splicing in Human Muscle," Human Gene Therapy, vol. 18 (9), pp. 798-810, 2007.
Aronin, "Expanded CAG repeats in the crosshairs," Nature Biotech. 27(5):451-452 (2009).
Arruda, V.R., "The Role of Immunosuppression in Gene- and Cell-Based Treatments for Duchenne Muscular Dystrophy," Molecular Therapy, vol. 15, No. 6, pp. 1040-1041, Jun. 2007.
Arzumanov, A., et al., "Inhibition of HIV-1 Tat-Dependent Trans Activation by Steric Block Chimeric 2'-0-Methyl/LNA Oligoribonucleotides," Biochemistry, 2001, vol. 40 (48), pp. 14645-14654.
ATDBio, "DNA duplex stability," www.atdbio.com/content/53/DNA-dupex-stability, 10 pages, Jun. 2014.
Austin, R.C., et al., "Cloning and Characterization of Alternatively Spliced Isoforms of Dp71," Human Molecular Genetics, 1995, vol. 4 (9), pp. 1475-1483.
Austin, R.C., et al., "Expression and Synthesis of Alternatively Spliced Variants Of Dp71 in Adult Human Brain," Neuromuscular Disorders, 2000, vol. 1 O (3), pp. 187-193.
Australian Government, IP Australia, Office Action for Australian Patent Application No. 2009240879, 3 pages, Jun. 22, 2011.
AVI Biopharma, Inc., Notice of Opposition filed against EP1619249, 47 pages, Jun. 23, 2009.
AVI Biopharma, Inc., Request for UK IPO Opinion (Section 74A & Rule 93)—EP(UK) 1619249, 24 pages, Mar. 9, 2009.
Barabino, S.M., et al., "Antisense Probes Targeted to an Internal Domain in U2 snRNP Specifically Inhibit the Second Step of Pre-mRNA Splicing," Nucleic Acids Research, 1992, vol. 20 (17), pp. 4457-4464.
Barany, F., "The Ligase Chain Reaction in a PCR World," PCR Methods and Applications, 1991, vol. 1 (1), pp. 5-16.
Bijvoet, A.G., et al., "Recombinant Human Acid a-Glucosidase: High Level Production in Mouse Milk, Biochemical Characteristics, Correction of Enzyme Deficiency in GSDII KO Mice.," Human Molecular Genetics, 1998, vol. 7 (11), pp. 1815-1824.
bionity.com, "Leiden University Medical Center and Prosensa B.V. Announce First Successful Clinical Study with RNA-based Therapeutic PR0051," Jan. 3, 2008, 1 page, http://www.bionity.com/news/e/76185.

(56) References Cited

OTHER PUBLICATIONS

Biopharmaceutiques, Merging Pharma & Biotech, Edition 48, 3 pages, Jan. 10, 2008, http://www.biogharmaceutigues.com/en/num/48.html.

Biospace, "Leiden University Medical Center and ProSensa B.V. Announce The New England Journal of Medicine Publication of First Successful Clinical Study with RNA-based Therapeutic PR0051 in Duchenne Muscular Dystrophy," 2 pages, http://www.biosgace.com/news_grint.asgx?NewsEntityID=81383. Dec. 27, 2007.

Boado, R., et al., "Antisense-Mediated Down-Regulation of the Human Huntingtin Gene," The Journal of Pharmacology and Experimental Therapeutics, vol. 295, No. 1, pp. 239-243, 2000.

Bonifazi et al., "Use of RNA Fluorescence In Situ Hybridization in the Prenatal Molecular Diagnosis of Myotonic Dystrophy Type I," Clinical Chemistry, Technical Briefs, vol. 52, Issue No. 2, pp. 319-322, 2006.

Bremmer-Bout, M., et al., "Targeted Exon Skipping in Transgenic hDMD Mice: A Model for Direct Preclinical Screening of Human-Specific Antisense Oligonucleotides," Molecular Therapy, vol. 10, No. 2, pp. 232-240, Aug. 2004.

Brett, D., et al., "EST Comparison Indicates 38% of Human mRNAs Contain Possible Alternative Splice Forms," FEBS Letters, vol. 474 (1), pp. 83-86, 2000.

Brown, M.D., et al., "Gene Delivery with Synthetic (Non Viral) Carriers," International Journal of Pharmaceutics, vol. 229 (1-2), pp. 1-21, 2001 (Abstract).

Buck, G.A., et al., "Design Strategies and Performance of Custom DNA Sequencing Primers," BioTechniques, vol. 27 (3), pp. 528-536, 1999.

Buczko et al., "Modulation of plasminogen activator inhibitor type-I biosynthesis in vitro and in vivo with oligo(nucleoside phosphorothioate )s and related constructs," Pharmacol. Ther., vol. 76, Issue Nos. 1-3, pp. 161-175, Oct.-Dec. 1997.

Burnett, R., et al., "DNA Sequence-Specific Polyamides Alleviate Transcription Inhibition Associated with Long GAA•TTC Repeats in Friedreich's Ataxia," Proceedings of the National Academy of Sciences of the United States of America, 2006, vol. 103 (31), pp. 11497-11502.

Canadian Intellectual Proper TY Office, Office Action for Canadian Patent Application No. 2,524,255, 2 pages, Jul. 6, 2011.

Caplen et al., "Rescue of polyglutamine-mediated cytotoxicity by double-stranded RNA-mediated RNA interference," Hum. Mol. Genet. 11(2):175-184 (2002).

Cartegni, L., et al., "Listening to Silence and Understanding Nonsense: Exonic Mutations that Affect Splicing," Nature Review Genetics, 2002, vol. 3 (4), pp. 285-298.

Chaubourt, E., et al., "Muscular Nitric Oxide Synthase (muNOS) and Utrophin," Journal of Physiology Paris, 2002, vol. 96 (1-2), pp. 43-52.

Cooper et al., "Molecular Biology. Neutralizing Toxic RNA," Science, vol. 325, Issue No. 5938, pp. 272-273, Jul. 2009.

Coulter, L.R., et al., "Identification of a New Class of Exonic Splicing Enhancers by In Vivo Selection," Molecular and Cellular Biology, 1997, vol. 17 (4), pp. 2143-2150.

Crooke, S.T., "Basic Principles of Antisense Therapeutics, Handbook of Experimental Pharmacology: Antisense Research and Application," Springer-Verlag Berlin Heidelberg, 1998, vol. 131, pp. 1-50.

Dahlqvist et al., "Functional Notch signaling is required for BMP4-induced inhibition of myogenic differentiation," Development 130(24):6089-6099 (2003).

Deangelis, F.G., et al., "Chimeric snRNA Molecules Carrying Antisense Sequences Against The Splice Junctions of Exon 51 of the Dystrophin Pre- mRNAInduce Exon Skipping and Restoration of a Dystrophin Synthesis in 848-50 DMD Cells," Proceedings of the National Academy of Sciences of the United States of America, Jul. 9, 2002, vol. 99 (14), pp. 9456-9461.

Denny, P., et al., "Oligo-Riboprobes. Tools for in Situ Hybridization," Histochemistry, 1988, vol. 89 (5), pp. 481-483.

Devor et al., "Oligonucleotide Yield, Resuspension, and Storage," Integrated DNA Technologies, 11 pages, 2005.

Dickson, G., et al., "Screening for Antisense Modulation of Dystrophin Pre-mRNA Splicing," Neuromuscular Disorders, 2002, vol. 12 (Suppl 1), pp. S67-S70.

Dirksen, W.P., et al., "Mapping the SF2/ASF Binding Sites in the Bovine Growth Hormone Exonic Splicing Enhancer," The Journal of Biological Chemistry, 2000, vol. 275 (37), pp. 29170-29177.

Duboc, D., et al., "Effect of Perindopril on the Onset and Progression of Left Ventricular Dysfunction in Duchenne Muscular Dystrophy," Journal of the American College of Cardiology, 2005, vol. 45 (6), pp. 855-857.

Dunckley, M.G., et al., "Modification of Splicing in the Dystrophin Gene in Cultured Mdx Muscle Cells by Antisense Oligoribonucleotides," Human Molecular Genetics, 1995, vol. 5 (1), pp. 1083-1090.

Dunckley, M.G., et al., "Modulation of Splicing in the DMD Gene by Antisense Oligoribonucleotides," Nucleosides & Nucleotides, 1997, vol. 16 (7-9), pp. 1665-1668.

Eder et al., "Inhibition of LNCaP prostate cancer cells by means of androgen receptor antisense oligonucleotides," Cancer Gene Ther., vol. 7, Issue No. 7, pp. 997-1007, 2000.

Erba, H.P., et al., "Structure, Chromosome Location, and Expression of the Human y-Actin Gene: Differential Evolution, Location, and Expression of the Cytoskeletal 13- and y-Actin Genes," Molecular and Cellular Biology, 1988, vol. 8 (4), pp. 1775-1789.

Errington, S.J., et al., "Target Selection for Antisense Oligonucleotide Induced Exon Skipping in the Dystrophin Gene," The Journal of Gene Medicine, 2003, vol. 5 (6), pp. 518-527.

European Patent Office, European Search Report, Annex, Application No. EP 03077205, dated Dec. 10, 2003, 6 pages.

European Patent Office, International Search Report, International Application No. PCT/NL2008/050673, dated Feb. 9, 2009, 8 pages.

European Patent Office, Office Action for European Patent Application No. EP05076770.6, 5 pages, dated Jan. 29, 2007.

Evers et al., "Targeting Several CAG Expansion Diseases by a Single Antisense Oligonucleotide," PLOS One, vol. 6, Issue No. 9, pp. e24308-1-e24308-11, Sep. 2011.

Federal Angecy for Medicines and Heal Th Products, Letter from Federal Agency for Medicines and Health Products to Prosensa, regarding a Phase 1/11, open label, escalating dose, pilot study to assess the effect, safety, tolerability and pharmacokinetics of multiple subcutaneous doses of PR0051 in patients with Duchenne muscular dystrophy, 2 pages, Jan. 9, 2008.

Feener, C.A., et al., "Alternative Splicing of Human Dystrophin mRNA Generates Isoforms at the Carboxy Terminus," Nature, 1989, vol. 338 (6215), pp. 509-511.

Fiszer et al., "An evaluation of oligonucleotide-based therapeutic strategies for polyQ diseases," BMC Mal. Biol., vol. 13, Issue No. 6, 12 pages, 2012.

Fluiter, K., et al., "In Vivo Tumor Growth Inhibition and Biodistribution Studies of Locked Nucleic Acid (LNA) Antisense Oligonucleotides," Nucleic Acids Research, 2003, vol. 31 (3), pp. 953-962.

Folini et al., "Antisense oligonucleotide-mediated inhibition of hTERT, but not hTERC, induces rapid cell growth decline and apoptosis in the absence of telomere shortening in human prostate cancer cells," Eur. J. Cancer, vol. 41, Issue No. 4, pp. 624-634, Mar. 2005.

Fu et al., "An Unstable Triplet Repeat in a Gene Related to Myotonic Muscular Dystrophy," Science, vol. 255, pp. 1256-1258, Mar. 1992.

Furling et al., "Viral vector producing antisense RNA restores myotonic dystrophy myoblast functions," Gene Therapy, vol. 10, pp. 795-802, 2003.

Gagnon et al., "Allele-Selective Inhibition of Mutant Huntington Expression with Antisense Oligonucleotides Targeting the Expanded CAG Repeat," Biochemistry, vol. 49, pp. 10166-10178, 2010.

Galderisi et al., "Myotonic Dystrophy: Antisense Oligonucleotide Inhibition of DMPK Gene Expression in Vitro," Biochem. Bioph. Res. Co., vol. 221, pp. 750-754, 1996.

Garcia-Blanco, M.A., et al., "Alternative Splicing in Disease and Therapy," Nature Biotechnology, May 2004, vol. 22 (5), pp. 535-546.

Genbank, Accession No. AZ993191.1, 2M0278E12F Mouse 10kb plasmid UUGC2M library Mus muscu genomic clone

(56) References Cited

OTHER PUBLICATIONS

UUGC2M0278E12 F, genomic survey sequence, entry created and last updated on Apr. 27, 2001, 2 pages.
Genbank, Accession No. EW162121.1, rfat0126_k17 .y1 fat Sus scrofa cDNA 5-, mRNA sequence, entry created on Aug. 13, 2007, last updated on Mar. 3, 2011, 2 pages.
Ghosh, P., et al., "Mannose 6-Phosphate Receptors: New Twists in the Tale," Natural Reviews Molecular Cell Biology, Mar. 2003, vol. 4 (3), pp. 202-212.
Ginjaar, I.B., et al., "Dystrophin Nonsense Mutation Induces Different Levels of Exon 29 Skipping and Leads to Variable Phenotypes within One BMD Family," European Journal of Human Genetics, 2000, vol. 8 (10), pp. 793-796.
Gollins et al., "High-efficiency plasmid gene transfer into dystrophic muscle," Gene Ther. 10(6):504-512 (2003).
Grady, D., "Early Drug Test Shows Promise in Treating Muscular Dystrophy," International Herald Tribune, Jan. 2008, Health and Science, p. 9.
Grady, D., Promising Dystrophy Drug Clears Early Test, The New York Times, 2 pages, Dec. 27, 2007.
Granchelli, J.A., et al., "Pre-Clinical Screening of Drugs Using the mdx Mouse," Neuromuscular Disorders, 2000, vol. 10(4-5), pp. 235-239.
Gryaznov, S.M., "Oligonucleotide N3'—PS' Phosphoramidates as Potential Therapeutic Agents," Biochimica et Biophysica Acta, 1999, vol. 1489, pp. 131-140.
Hagiwara, Y., et al., "A Novel Point Mutation (G$^{-1}$To T) In A 5' Splice Donor Site of Intron 13 Of The Dystrophin Gene Results in Exon Skipping and is Responsible for Becker Muscular Dystrophy.," American Journal of Human Genetics, 1994, vol. 54 (1), pp. 53-61.
Hansen, S., "Product Development—Addition by subtraction," BioCentury, The Bernstein Report on BioBusiness, Jan. 7, 2008, p. A28.
Harrison et al., "Synthesis and hybridization analysis of a small library of peptide-oligonucleotide conjugates," Nucleic Acids Research, vol. 26, No. 13, pp. 3136-3145, 1998.
Hasholt et al., "Antisense downregulation of mutant huntingtin in a cell model," J. Gene Med., vol. 5, pp. 528-538, 2003.
Hassan, A.B., "Keys to the Hidden Treasures of the Mannose 6-Phosphate/Insulin-Like Growth Factor 2 Receptor," American Journal of Pathology, Jan. 2003, vol. 162 (1), pp. 3-6.
Heemskerk, H., et al., "Development of Antisense-Mediated Exon Skipping as a Treatment for Duchenne Muscular Dystrophy," Annals of the New York Academy of Sciences, 2009, vol. 1175, pp. 71-79.
Heemskerk, H.A., et al., "Preclinical PK and PD Studies on 2'-O-Methyl—phosphorothioate RNA Antisense Oligonucleotides in the mdx Mouse Model," Molecular Therapy, Jun. 2010, vol. 18 (6), pp. 1210-1217.
Highfield, R., "Roger Highfield rounds up latest snippets of science, from a new treatment for muscular dystrophy, detecting tumours to the benefits of cooking vetables," Science: Boffin log, Jan. 1, 2008, 5 pages.
Hoffman, E.P., "Skipping Toward Personalized Molecular Medicine," The New England Journal of Medicine, Dec. 2007, vol. 357 (26), pp. 2719-2722.
Hoffman, E.P., et al., "Somatic Reversion/Suppression of the Mouse mdx Phenotype in Vivo," Journal of the Neurological Sciences, 1990, vol. 99 (1), pp. 9-25.
Hussey, N.D., et al., "Analysis of Five Duchenne Muscular Dystrophy Exons and Gender Determination Using Conventional Duplex Polymerase Chain Reaction on Single Cells," Molecular Human Reproduction, 1999, vol. 5 (11), pp. 1089-1094.
Iezzi, S., et al, "Deacetylase Inhibitors Increase Muscle Cell Size by Promoting Myoblast Recruitment and Fusion through Induction of Follistatin," Developmental Cell, May 2004, vol. 6(5), pp. 673-684.
Ikezawa, M., et al., "Dystrophin Gene Analysis on 130 Patients with Duchenne Muscular Dystrophy with a Special Reference to Muscle mRNA Analysis," Brain & Development, 1998, vol. 20 (3), pp. 165-168.
International Preliminary Examining Authority—European Patent Office, International Preliminary Examination Report for International Application No. PCT/NL01/00697, 2 pages, dated Aug. 1, 2002.
International Searching Authority—European Patent Office, International Preliminary Report on Patentability and Written Opinion, International Application No. PCT/EP2007/054842, dated Nov. 21, 2008, 8 pages.
International Searching Authority—European Patent Office, International Search Report, International Application No. PCT/EP2007/054842 3 pages, dated Aug. 21, 2007.
International Searching Authority—European Patent Office, International Search Report, International Application No. PCT/NL01/00697, 2 pages, dated Dec. 21, 2001.
International Searching Authority—European Patent Office, International Search Report, International Application No. PCT/NL2004/000196, 7 pages, dated Dec. 10, 2004.
International Searching Authority—European Patent Office, International Search Report, International Application No. PCT/NL2006/000209, 4 pages, dated Oct. 5, 2006.
International Searching Authority—European Patent Office, International Search Report, International Application No. PCT/NL2008/050470, 4 pages, dated Jul. 2, 2009.
International Searching Authority—European Patent Office, International Search Report, International Application No. PCT/NL2008/050475, 30 pages, dated Jun. 25, 2009.
International Searching Authority—European Patent Office, International Search Report, International Application No. PCT/NL2009/050006, 5 pages, dated Jul. 31, 2009.
International Searching Authority—European Patent Office, International Search Report, International Application No. PCT/NL2009/050113, 8 pages, dated Jun. 30, 2010.
Ito, T., et al., "Purine-Rich Exon Sequences are Not Necessarily Splicing Enhancer Sequence in the Dystrophin Gene," The Kobe Journal of Medical Sciences, Oct. 2001, vol. 47 (5), pp. 193-202.
Kandimalla et al., "Effects of phosphorothioate oligodeoxyribonucleotide and oligoribonucleotides on human complement and coagulation," Bioorg. Med. Chem. Lett., vol. 8, Issue No. 16, pp. 2103-2108, 1998.
Karras, J.G., et al., "Deletion of Individual Exons and Induction of Soluble Murine Interleukin-5 Receptor-a Chain Expression through Antisense Oligonucleotide-Mediated Redirection of Pre-mRNA Splicing," Molecular Pharmacology, 2000, vol. 58 (2), pp. 380-387.
Katholieke Universiteit Leuven, Letter from Katholieke Universiteit Leuven to Dr. N. Goemans, Child Neurology regarding Study Phase 1/11, PR0051-02, 5 pages, dated Jan. 22, 2008 (translation provided).
Kerr, K., et al., "BMP Regulates Skeletal Myogenesis at Two Steps," Molecular and Cellular Proteomics, 2003, vol. 2 (9), pp. 976.
Kinali, M., et al., "Local Restoration of Dystrophin Expression With the Morpholino Oligomer AV1-4658 in Duchenne Muscular Dystrophy: A Single-Blind, Placebo-Controlled, Dose-Escalation, Proof-of-Concept Study," The Lancet. Neurology, 2009, vol. 8 (10), pp. 918-928.
Krainer, A., Declaration of Dr. Adrian Krainer, 7 pages, Jul. 21, 2010, (submitted in Third Party's Statement for JP Application No. 2002-529499 on Oct. 29, 2010).
Kurreck, J., et al., "Design of Antisense Oligonucleotides Stabilized by Locked Nucleic Acids," Nucleic Acids Research, 2002, vol. 30 (9), pp. 1911-1918.
Langlois, M.A., et al., "Hammerhead Ribozyme-Mediated Destruction of Nuclear Foci in Myotonic Dystrophy Myoblasts," Molecular Therapy, 2003, vol. 7 (5), pp. 670-680.
Laptev, AV., et al., "Specific Inhibition of Expression of a Human Collagen Gene (COL 1A1) with Modified Antisense Oligonucleotides. The Most Effective Target Sites are Clustered in Double Stranded Regions of the Predicted Secondary Structure for the mRNA," Biochemistry, 1994, vol. 33 (36), pp. 11033-11039.
Lebedev et al., "Oligonucleotides containing 2-aminoadenine and 5-methycytosine are more effective as primers for PCR amplification than their non-modified counterparts," Genet. Anal., vol. 13, No. 1, pp. 15-21 (Abstract).

(56) References Cited

OTHER PUBLICATIONS

Lee et al., "RNase H-mediated degradation of toxic RNA in myotonic dystrophy type 1," P. Natl. Acad. Sci. USA, vol. 109, Issue No. 11, pp. 4221-4226, Mar. 2012.

Lee, J.H., et al., "Receptor Mediated Uptake of Peptides that Bind the Human Transferrin Receptor," European Journal of Biochemistry/ FEBS, 2001, vol. 268 (7), pp. 2004-2012.

Lewin, B., "Genes VII," Oxford University Press, 2000, Chapters: 1, 5, 22; pp. 29, 126, 129, 686, 704, 705.

Liu et al., "Specific inhibition of Huntington's disease gene expression by siRNAs in cultured cells," Proc. Japan Acad. Ser. B, vol. 79B, pp. 293-298, 2003.

Liu, H.X., et al., "A Mechanism for Exon Skipping Caused by Nonsense or Missense Mutations in BRCA1 and Other Genes," Nature Genetics, Jan. 2001, vol. 27 (1), pp. 55-58.

Liu, H.X., et al., "Identification of Functional Exonic Splicing Enhancer Motifs Recognized by Individual SR Proteins," Genes & Development, 1998, vol. 12 (13), pp. 1998-2012.

Lu, Q.L., et al., "Functional Amounts of Dystrophin Produced by Skipping the Mutated Exon in the mdx Dystrophic Mouse," Nature Medicine, Aug. 2003, vol. 9 (8), pp. 1009-1014.

Lu, Q.L., et al., "Massive Idiosyncratic Exon Skipping Corrects the Nonsense Mutation in Dystrophic Mouse Muscle and Produces Functional Revertant Fibers by Clonal Expansion," The Journal of Cell Biology, 2000, vol. 148 (5), pp. 985-995.

Lu, Q.L. et al., "Non-Viral Gene Delivery in Skeletal Muscle: A Protein Factory," Gene Therapy, 2003, vol. 10 (2), pp. 131-142.

Lu, Q.L., et al., "Systemic Delivery of Antisense Oligoribonucleotide Restores Dystrophin Expression in Body-Wide Skeletal Muscles," Proceedings of the National Academy of Sciences of the United States of America, Jan. 2005, vol. 102 (1), pp. 198-203.

Magana et al., "Perspectives on Gene Therapy in Myotonic Dystrophy Type 1," J. Neurosci. Res., vol. 89, pp. 275-285, 2011.

Mann, C.J., et al., "Antisense-Induced Exon Skipping and Synthesis of Dystrophin in the mdx Mouse," Proceedings of the National Academy of Sciences of the United States of America, Jan. 2001, vol. 98 (1), pp. 42-47.

Mann, C.J., et al., "Improved Antisense Oligonucleotide Induced Exon Skipping in the mdx Mouse Model of Muscular Dystrophy," The Journal of Gene Medicine, 2002, vol. 4 (6), pp. 644-654.

Martiniuk, F., et al., "Correction of Glycogen Storage Disease Type II by Enzyme Replacement with a Recombinant Human Acid Maltase Produced by Over-Expression in a CHO-DHFR(Neg) Cell Line," Biochemical and Biophysical Research Communications, Oct. 2000, vol. 276 (3), pp. 917-923 (Abstract).

Matsuo, M., "Duchenne/Becker Muscular Dystrophy: From Molecular Diagnosis to Gene Therapy," Brain & Development, 1996, vol. 18 (3), pp. 167-172.

Matsuo, M., et al., "Exon Skipping during Splicing of Dystrophin mRNA Precursor due to an Intraexon Deletion in the Dystrophin Gene of Duchenne Muscular Dystrophy Kobe," The Journal of Clinical Investigation, 1991, vol. 87 (6), pp. 2127-2131.

Matsuo, M., et al., "Partial Deletion of a Dystrophin Gene Leads to Exon Skipping and to Loss of an Intra-Exon Hairpin Structure from the Predicted mRNA Precursor," Biochemical and Biophysical Research Communications, 1992, vol. 182 (2), pp. 495-500.

Mcclorey, G., et al., "Induced Dystrophin Exon Skipping in Human Muscle Explants," Neuromuscular Disorders, 2006, vol. 16 (9-10), pp. 583-590.

Medical News Today, "New Clinical Trial Results Show How Personalized Medicine Will Alter Treatment of Genetic Disorders," http://www.medicalnewstoday.com/releases/92777.QhQ. 2 pages, Dec. 29, 2007.

Monaco, A.P., et al., "An Explanation for the Phenotypic Differences between Patients Bearing Partial Deletions of the DMD Locus," Genomics, 1988, vol. 2 (1), pp. 90-95.

Moon, I.J., et al., "Target Site Search and Effective Inhibition of Leukaemic Cell Growth by a Covalently Closed Multiple Anti-Sense Oligonucleotide to c-myb," The Biochemical Journal, 2000, vol. 346, pp. 295-303.

Mulders et al., "Molecular therapy in myotonic dystrophy: focus on RNA gain-of-function," Hum. Mal. Gen., vol. 19, Review Issue No. 1, pp. R90-R97, 2010.

Mulders et al., "Triplet-repeat oligonucleotide-mediated reversal of RNA toxicity in myotonic dystrophy," Proceedings of the National Academy of Sciences of the U.S.A., vol. 106, No. 33, pp. 13915-13920, Aug. 2009.

Munroe, S.H., "Antisense RNA Inhibits Splicing of Pre-mRNA in Vitro," The EMBO Journal, 1988, vol. 7 (8), pp. 2523-2532.

Muntoni et al., "Targeting RNA to treat neuromuscular disease," Nature Rev. Drug Discov., vol. 10, pp. 621-637, Aug. 2011.

Muntoni, F., et al., "149th ENMC International Workshop and 1st Treat-NMD Workshop on: "Planning Phase 1 /11 Clinical trials using Systemically Delivered Antisense Oligonucleotides in Duchenne Muscular Dystrophy"," Neuromuscular Disorders, 2008, vol. 18, pp. 268-275.

Muntoni, F., et al., "A Mutation in the Dystrophin Gene Selectively Affecting Dystrophin Expression in the Heart," The Journal of Clinical Investigation, Aug. 1995, vol. 96 (2), pp. 693-699.

Nakamori et al., "Stabilization of Expanded (CTG)•(CAG) Repeats by Antisense Oligonucleotides," Mal. Ther., vol. 19, Issue No. 12, pp. 2222-2227, Dec. 2011.

Nederlandsch Octrooibureau, Patentee's response to communication dated Jul. 29, 2009 from the Opposition Division of EPO in relation to European Patent Application (EP 05 076 770.6), dated Jan. 27, 2010, 41 pages.

Nishio, H., et al., "Identification of a Novel First Exon in the Human Dystrophin Gene and of a New Promoter Located More Than 500 Kb Upstream of the Nearest Known Promoter," The Journal of Clinical Investigation, 1994, vol. 94 (3), pp. 1037-1042.

Opalinska, J.B., et al., "Nucleic-Acid Therapeutics: Basic Principles and Recent Applications," Nature Reviews. Drug Discovery, Jul. 2002, vol. 1 (7), pp. 503-514.

O'Shaughnessy, J., et al., "Superior Survival With Capecitabine Plus Docetaxel Combination Therapy in Anthracycline-Pretreated Patients With Advanced Breast Cancer: Phase 111 Trial Results," Journal of Clinical Oncology, 2002, vol. 20 (12), pp. 2812-2823.

Oxford Dictionary of English, 2nd Edition, Revised, Oxford University Press, p. 158, 2005.

Patel, K., et al., "The Function of Myostatin and Strategies Of Myostatin Blockade-New Hope for Therapies Aimed at Promoting Growth of Skeletal Muscle," Neuromuscular Disorders, 2005, vol. 15 (2), pp. 117-126.

Politano, L., et al., "Gentamicin Administration in Duchenne Patients With Premature Stop Codon. Preliminary Results," Acta Myologica, 2003, vol. 22 (1), pp. 15-21.

Popplewell, L.J., et al., "Design of Phosphorodiamidate Morpholino Oligomers (PMOs) for the Induction of Exon Skipping of the Human DMD Gene," Molecular Therapy, Mar. 2009, vol. 17 (3), pp. 554-561.

Pramono, Z.A., et al., "Induction of Exon Skipping of the Dystrophin Transcript in Lymphoblastoid Cells by Transfecting an Antisense Oligodeoxynucleotide Complementary to an Exon Recognition Sequence," Biochemical and Biophysical Research Communications, 1996, vol. 226 (2), pp. 445-449.

Radley, H.G., et al., "Duchenne Muscular Dystrophy: Focus on Pharmaceutical and Nutritional Interventions," The International Journal of Biochemistry & Cell Biology, 2007, vol. 39 (3), pp. 469-477.

Randa et al. "The AUUCU Repeats Responsible for Spinocerebellar Ataxia Type 10 Form Unusual RNA Hairpins," J. Biol. Chem., vol. 280, Issue No. 32, pp. 29340-29345, 2005.

Rando, T.A., "Oligonucleotide-Mediated Gene Therapy for Muscular Dystrophies," Neuromuscular Disorders, 2002, vol. 12 (Suppl 1), pp. S55-S60.

Redorbit News, "LUMC and Prosensa Report Positive Results of DMD Study," Dec. 28, 2007, 1 page.

Reitter, B., "Deflazacort vs. Prednisone in Duchenne Muscular Dystrophy: Trends of an Ongoing Study," Brain & Development, 1995, vol. 17 Suppl, pp. 39-43.

Reuser, A.J., et al., "Uptake and Stability of Human and Bovine Acid a-Glucosidase in Cultured Fibroblasts and Skeletal Muscle

(56) References Cited

OTHER PUBLICATIONS

Cells from Glycogenosis Type 11 Patients," Experimental Cell Research, 1984, vol. 155 (1), pp. 178-189.
Roberts, R.G., et al., "Direct Detection of Dystrophin Gene Rearrangements by Analysis of Dystrophin mRNA in Peripheral Blood Lymphocytes," American Journal of Human Genetics, 1991, vol. 49 (2), pp. 298-310.
Roberts, R.G., et al., "Direct Diagnosis of Carriers of Duchenne and Becker Muscular Dystrophy by Amplification of Lymphocyte RNA," Lancet, 1990, vol. 336 (8730), pp. 1523-1526.
Roberts, R.G., et al., "Searching for the 1 in 2,400,000: A Review of Dystrophin Gene Point Mutations," Human Mutation, 1994, vol. 4 (1), pp. 1-11.
Roberts, R.G., et al., "Exon Structure on the Human Dystrophin Gene," Genomics, 1993, vol. 16(2), pp. 536-538.
Rolland, J.F., et al., "Overactivity of Exercise-Sensitive Cation Channels and their Impaired Modulation by IGF-1 in mdx Native Muscle Fibers: Beneficial Effect of Pentoxifylline," Neurobiology of Disease, 2006, vol. 24 (3), pp. 466-474.
Sah et al., "Oligonucleotide therapeutic approaches for Huntington disease," J. Clin. Invest. 12(2):500-507 (2011).
Samoylova, T., et al., "Elucidation of Muscle-Binding Peptides by Phage Display Screening," Muscle & Nerve, Apr. 1999, vol. 22(4), pp. 460-466.
Scanlon, K.J., "Anti-Genes: siRNA, Ribozymes and Antisense," Current Pharmaceutical Biotechnology, 2004, vol. 5 (5), pp. 415-420.
Segalat, L., et al., "CAPON Expression in Skeletal Muscle is Regulated by Position, Repair, NOS Activity, and Dystrophy," Experimental Cell Research, 2005, vol. 302 (2), pp. 170-179.
Sertic, J., et al., "Deletion Screening of the Duchenne/Becker Muscular Dystrophy Gene in Croatian Population," Collegium Antropologicum, 1997, vol. 21 (1), pp. 151-156.
Shapiro, M.B., et al., "RNA Splice Junctions of Different Classes of Eukaryotes: Sequence Statistics and Functional Implications in Gene Expression," Nucleic Acids Research, 1987, vol. 15 (17), pp. 7155-7174.
Sherratt, T.G., et al., "Exon Skipping and Translation in Patients with Frameshift Deletions in the Dystrophin Gene," American Journal of Human Genetics, 1993, vol. 53 (5), pp. 1007-1015.
Shiga, N., et al., "Disruption of the Splicing Enhancer Sequence within Exon 27 of the Dystrophin Gene by a Nonsense Mutation Induces Partial Skipping of the Exon and is Responsible for Becker Muscular Dystrophy," The Journal of Clinical Investigation, Nov. 1997, vol. 100 (9), pp. 2204-2210.
Simoes-Wust, A.P., et al., "bcl-xL Antisense Treatment Induces Apoptosis in Breast Carcinoma Cells," International Journal of Cancer, 2000, vol. 87 (4), pp. 582-590.
Smith, B.F., et al., "Muscle-specific Peptide #5," XP-002442550, 1 pages, Mar. 23, 1999.
Spitali, P., et al., "Exon Skipping-Mediated Dystrophin Reading Frame Restoration for Small Mutations," Human Mutation, vol. 30(11), pp. 1527-1534, 2009.
Squires, K.E. "An Introduction to Nucleoside and Nucleotide Analogues," Antiviral Therapy, 6 (Suppl. 3), pp. 1-14, 2001.
Sterrenburg, E., et al., "Gene Expression Profiling Highlights Defective Myogenesis in DMD Patients and a Possible Role for Bone Morphogenetic Protein 4," Neurobiology of Disease, vol. 23 (1), pp. 228-236, 2006.
Surono, A., et al., "Chimeric RNA/Ethylene-Bridged Nucleic Acids Promote Dystrophin Expression in Myocytes of Duchenne Muscular Dystrophy by Inducing Skipping of the Nonsense Mutation-Encoding Exon," Human Gene Therapy, 2004, vol. 15 (8), pp. 749-757.
Surono, A., et al., "Six Novel Transcripts that Remove a Huge Intron Ranging from 250 to 800 kb are Produced by Alternative Splicing of the 5' Region of the Dystrophin Gene in Human Skeletal Muscle," Biochemical and Biophysical Research Communications, 1997, vol. 239 (3), pp. 895-899.
Suter, D., et al., "Double-Target Antisense U7 snRNAs Promote Efficient Skipping of an Aberrant Exon in Three Human -Thalassemic Mutations," Human Molecular Genetics, 1999, vol. 8 (13), pp. 2415-2423.
Suwanmanee, T., et al., "Restoration of Human -Globin Gene Expression in Murine and Human IVS2-654 Thalassemic Erythroid Cells by Free Uptake of Antisense Oligonucleotides," Molecular Pharmacology, 2002, vol. 62 (3), pp. 545-553.
Takeshima, Y., et al., "Intravenous Infusion of an Antisense Oligonucleotide Results in Exon Skipping in Muscle Dystrophin mRNA of Duchenne Muscular Dystrophy," Pediatric Research, 2006, vol. 59 (5), pp. 690-694.
Takeshima, Y., et al., "Modulation of In Vitro Splicing of the Upstream Intron by Modifying an Intra-Exon Sequence Which is Deleted from the Dystrophin Gene in Dystrophin Kobe," The Journal of Clinical Investigation, Feb. 1995, vol. 95 (2), pp. 515-520.
Takeshima, Y., et al., "Oligonucleotides Against a Splicing Enhancer Sequence Led to Dystrophin Production In Muscle Cells from a Duchenne Muscular Dystrophy Patient," Brain& Development, 2001, vol. 23 (8), pp. 788-790.
Tanaka, K., et al., "Polypurine Sequences within a Downstream Exon Function as a Splicing Enhancer," Molecular and Cellular Biology, 1994, vol. 14 (2), pp. 1347-1354.
Taneja, "Localization of Trinucleotide Repeat Sequences in Myotonic Dystrophy Cells Using a Single Fluorochrome-Labeled PNA Probe," Biotechniques, vol. 24, Issue No. 3, pp. 472-476, Mar. 1998.
Thanh, L.T., et al., "Characterization of Revertant Muscle Fibers in Duchenne Muscular Dystrophy, Using Exon-Specific Monoclonal Antibodies against Dystrophin," American Journal of Human Genetics, 1995, vol. 56 (3), pp. 725-731.
Thomsen et al., "Dramatically improved RNA in situ hybridization signals using LNA-modifiedprobes," RNA, vol. 11, pp. 1745-1748, 2005.
Tian, H., et al., "Selection of Novel Exon Recognition Elements from a Pool of Random Sequences," Molecular and Cellular Biology, Nov. 1995, vol. 15 (11), pp. 6291-6298.
Treat-NMD, Neuromuscular Network, Newsletter No. 24, 6 pages, Jan. 11, 2008.
Tsuchida, K., "The Role of Myostatin and Bone Morphogenetic Proteins in Muscular Disorders," Expert Opinion of Biological Therapy, 2006, vol. 6 (2), pp. 147-154.
United States Patent and Trademark Office, Office Action for U.S. Appl. No. 11/233,495, dated Jun. 25, 2009, 11 pages.
United States Patent and Trademark Office, Office Action for U.S. Appl. No. 10/395,031, 11 pages, dated Apr. 2, 2009.
United States Patent and Trademark Office, Office Action for U.S. Appl. No. 10/395,031, 15 pages, dated Nov. 30, 2006.
United States Patent and Trademark Office, Office Action for U.S. Appl. No. 10/395,031, 16 pages, dated Feb. 6, 2006.
United States Patent and Trademark Office, Office Action for U.S. Appl. No. 10/395,031, 20 pages, dated Aug. 23, 2007.
United States Patent and Trademark Office, Office Action for U.S. Appl. No. 10/395,031, 20 pages, dated Jul. 8, 2005.
United States Patent and Trademark Office, Office Action for U.S. Appl. No. 10/395,031, 29 pages, dated May 30, 2008.
United States Patent and Trademark Office, Office Action for U.S. Appl. No. 10/395,031, 7 pages, dated Oct. 16, 2009.
United States Patent and Trademark Office, Office Action for U.S. Appl. No. 11/233,495, 14 pages, dated Dec. 1, 2008.
United States Patent and Trademark Office, Office Action for U.S. Appl. No. 11/233,507, 12 pages, dated Mar. 19, 2008.
United States Patent and Trademark Office, Office Action for U.S. Appl. No. 11/233,507, 16 pages, dated Jun. 15, 2007.
United States Patent and Trademark Office, Office Action for U.S. Appl. No. 11/233,507, 17 pages, dated May 29, 2009.
United States Patent and Trademark Office, Office Action for U.S. Appl. No. 11/233,507, 17 pages, dated Nov. 12, 2008.
United States Patent and Trademark Office, Office Action for U.S. Appl. No. 11/982,285, 16 pages, dated May 4, 2009.
United States Patent and Trademark Office, Office Action for U.S. Appl. No. 11/982,285, 22 pages, dated Sep. 18, 2009.

(56) References Cited

OTHER PUBLICATIONS

Van Deutekom, J.C., et al., "Advances in Duchenne Muscular Dystrophy Gene Therapy," Nature Reviews Genetics, Oct. 2003, vol. 4 (10), pp. 774-783.

Van Deutekom, J.C., et al., "Antisense-induced exon skipping restores dystrophin expression in DMD patient derived muscle cells," Human Molecular Genetics, vol. 10, No. 15, pp. 1547-1554, 2001.

Van Deutekom, J.C., et al., "Local Dystrophin Restoration with Antisense Oligonucleotide PR0051," The New England Journal of Medicine, 2007, vol. 357 (26), pp. 2677-2686.

Van Ommen, G.J., et al., "The Therapeutic Potential of Antisense-Mediated Exon Skipping," Current Opinion in Molecular Therapeutics, 2008, vol. 10 (2), pp. 140-149.

Van Vliet, L., et al., "Assessment of the Feasibility of Exon 45-55 Multiexon Skipping for Duchenne Muscular Dystrophy," BMC Medical Genetics, 2008, vol. 9 (105), 7 pages.

Varani, G., et al., "The G•U Wobble Base Pair. A Fundamental Building Block of RNA Structure Crucial to RNA Function in Diverse Biological Systems," EMBO Reports, 2000, vol. 1 (1), pp. 18-23.

Verreaul T, M., et al., "Gene Silencing in the Development of Personalized Cancer Treatment: The Targets, the Agents and the Delivery Systems," Current Gene Therapy, 2006, vol. 6 (4), pp. 505-533.

Vickers, T.A., et al., "Efficient Reduction of Target RNAs by Small Interfering RNA and RNase H-dependent Antisense Agents. A Comparative Analysis," The Journal of Biological Chemistry, Feb. 2003, vol. 278 (9), pp. 7108-7118.

Wang, B., et al., "Adeno-Associated Virus Vector Carrying Human Minidystrophin Genes Effectively Ameliorates Muscular Dystrophy in mdx Mouse Model," Proceedings of the National Academy of Sciences of the United States of America, 2000, vol. 97 (25), pp. 13714-13719.

Watakabe, A., et al., "The Role of Exon Sequences in Splice Site Selection," Genes & Development, 1993, vol. 7 (3), pp. 407-418.

Weisbart, R.H., et al., "Cell Type Specific Targeted Intracellular Delivery Into Muscle of a Monoclonal Antibody that Binds Myosin llb," Molecular Immunology, 2003, vol. 39 (13), pp. 783-789 (Abstract).

Wells, K.E., et al., "Enhanced in Vivo Delivery of Antisense Oligonucleotides to Restore Dystrophin Expression in Adult mdx Mouse Muscle," FESS Letters, 2003, vol. 552 (2-3), pp. 145-149.

Wenk, J., et al., "Quantitation of Mr 46000 and Mr 300000 Mannose 6-Phosphate Receptors in Human Cells and Tissues," Biochemistry International, 1991, vol. 23 (4), pp. 723-731 (Abstract).

Wheeler et al., "Reversal of RNA Dominance by Displacement of Protein Sequestered on Triplet Repeat RNA," Science, vol. 325, pp. 336-339, Jul. 2009.

Wheway, J.M., et al., "The Dystrophin Lymphocyte Promoter Revisited: 4.5-Megabase lntron, or Artefact?," Neuromuscular Disorders, 2003, vol. 13 (1), pp. 17-20.

Wilton, S.D., et al., "Antisense Oligonucleotides, Exon Skipping and the Dystrophin Gene Transcript.," Acta Myologica, 2005, vol. 24, pp. 222-229.

Wilton, S.D., et al., "Specific Removal of the Nonsense Mutation from the mdx Dystrophin mRNA Using Antisense Oligonucleotides," Neuromuscular Disorders, 1999, vol. 9 (5), pp. 330-338.

Yen, L., et al., "Sequence-specific Cleavage of Huntingtin mRNA by Catalytic DNA," Annals of Neurology, 1999, vol. 46 (3), pp. 366-373.

Zhang, G., et al., "Efficient Expression of Naked DNA Delivered lntraarterially to Limb Muscles of Nonhuman Primates," Human Gene Therapy, 2001, vol. 12 (4), pp. 427-438 (Abstract).

Zhou, G.Q., et al., "Current Understanding of Dystrophin-Related Muscular Dystrophy and Therapeutic Challenges Ahead," Chinese Medical Journal, 2006, vol. 119 (16), pp. 1381-1391.

Elayadi et al., "Application of PNA and LNA oligomers to chemotherapy," Curr. Opin. Investig. Drugs, 2(4):558-561 (2001).

Handa et al., "The AUUCU repeats responsible for spinocerebellar ataxia type 10 form unusual RNA hairpins," J. Biol. Chem., 280(32):29340-29345 (2005).

Sun et al., "Phosphorodiamidate morpholino oligomers suppress mutant huntingtin expression and attenuate neurotoxicity," Hum. Mol. Genet., 23(23):6302-6317 (2014).

TREATMENT OF GENETIC DISORDERS ASSOCIATED WITH DNA REPEAT INSTABILITY

PRIORITY

This application is a U.S. divisional application of U.S. patent application Ser. No. 14/809,483, filed Jul. 27, 2015, which is a divisional application of U.S. patent application Ser. No. 12/377,160, filed Feb. 24, 2010, which is a U.S. National Stage Entry of PCT/NL07/050399, filed on Aug. 10, 2007, which claims priority to EP 06118809.0, filed Aug. 11, 2006 and EP 06119247.2, filed Aug. 21, 2006, the disclosure of each of which is incorporated herein by reference in its entirety.

FIELD OF THE INVENTION

The current invention relates to the field of medicine, in particular to the treatment of genetic disorders associated with genes that have unstable repeats in their coding or non-coding sequences, most in particular unstable repeats in the human Huntington disease causing HD gene or the myotonic dystrophy type 1 causing DMPK gene.

BACKGROUND OF THE INVENTION

Instability of gene-specific microsatellite and minisatellite repetitive sequences, leading to increase in length of the repetitive sequences in the satellite, is associated with about 35 human genetic disorders. Instability of trinucleotide repeats is for instance found in genes causing X-linked spinal and bulbar muscular atrophy (SBMA), myotonic dystrophy type 1 (DM1), fragile X syndrome (FRAX genes A, E, F), Huntington's disease (HD) and several spinocerebellar ataxias (SCA gene family). Unstable repeats are found in coding regions of genes, such as the Huntington's disease gene, whereby the phenotype of the disorder is brought about by alteration of protein function and/or protein folding. Unstable repeat units are also found in untranslated regions, such as in myotonic dystrophy type 1 (DM1) in the 3' UTR or in intronic sequences such as in myotonic dystrophy type 2 (DM2). The normal number of repeats is around 5 to 37 for DMPK, but increases to premutation and full disease state two to ten fold or more, to 50, 100 and sometimes 1000 or more repeat units. For DM2/ZNF9 increases to 10,000 or more repeats have been reported. (Cleary and Pearson, Cytogenet. Genome Res. 100: 25-55, 2003).

The causative gene for Huntington's disease, HD, is located on chromosome 4. Huntington's disease is inherited in an autosomal dominant fashion. When the gene has more than 35 CAG trinucleotide repeats coding for a polyglutamine stretch, the number of repeats can expand in successive generations. Because of the progressive increase in length of the repeats, the disease tends to increase in severity and presents at an earlier age in successive generations, a process called anticipation. The product of the HD gene is the 348 kDa cytoplasmic protein huntingtin. Huntingtin has a characteristic sequence of fewer than 40 glutamine amino acid residues in the normal form; the mutated huntingtin causing the disease has more than 40 residues. The continuous expression of mutant huntingtin molecules in neuronal cells results in the formation of large protein deposits which eventually give rise to cell death, especially in the frontal lobes and the basal ganglia (mainly in the caudate nucleus). The severity of the disease is generally proportional to the number of extra residues.

DM1 is the most common muscular dystrophy in adults and is an inherited, progressive, degenerative, multisystemic disorder of predominantly skeletal muscle, heart and brain. DM1 is caused by expansion of an unstable trinucleotide (CTG)n repeat in the 3' untranslated region of the DMPK gene (myotonic dystrophy protein kinase) on human chromosome 19q (Brook et al, Cell, 1992). Type 2 myotonic dystrophy (DM2) is caused by a CCTG expansion in intron 1 of the ZNF9 gene, (Liguori et al, Science 2001). In the case of myotonic dystrophy type 1, the nuclear-cytoplasmic export of DMPK transcripts is blocked by the increased length of the repeats, which form hairpin-like secondary structures that accumulate in nuclear foci. DMPK transcripts bearing a long (CUG)n tract can form hairpin-like structures that bind proteins of the muscleblind family and subsequently aggregate in ribonuclear foci in the nucleus. These nuclear inclusions are thought to sequester muscleblind proteins, and potentially other factors, which then become limiting to the cell. In DM2, accumulation of ZNF9 RNA carrying the (CCUG)n expanded repeat form similar foci. Since muscleblind proteins are splicing factors, their depletion results in a dramatic rearrangement in splicing of other transcripts. Transcripts of many genes consequently become aberrantly spliced, for instance by inclusion of fetal exons, or exclusion of exons, resulting in non-functional proteins and impaired cell function.

The observations and new insights above have led to the understanding that unstable repeat diseases, such as myotonic dystrophy type 1, Huntington's disease and others can be treated by removing, either fully or at least in part, the aberrant transcript that causes the disease. For DM1, the aberrant transcript that accumulates in the nucleus could be down regulated or fully removed. Even relatively small reductions of the aberrant transcript could release substantial and possibly sufficient amounts of sequestered cellular factors and thereby help to restore normal RNA processing and cellular metabolism for DM (Kanadia et al., PNAS 2006). In the case of HD, a reduction in the accumulation of huntingtin protein deposits in the cells of an HD patient can ameliorate the symptoms of the disease.

A few attempts have been made to design methods of treatment and medicaments for unstable repeat disease myotonic dystrophy type 1 using antisense nucleic acids, RNA interference or ribozymes. (i) Langlois et al. (Molecular Therapy, Vol. 7 No. 5, 2003) designed a ribozyme capable of cleaving DMPK mRNA. The hammerhead ribozyme is provided with a stretch RNA complementary to the 3' UTR of DMPK just before the CUG repeat. In vivo, vector transcribed ribozyme was capable of cleaving and diminishing in transfected cells both the expanded CUG repeat containing mRNA as well as the normal mRNA species with 63 and 50% respectively. Hence, also the normal transcript is gravely affected by this approach and the affected mRNA species with expanded repeats are not specifically targeted.

(ii) Another approach was taken by Langlois et al., (Journal Biological Chemistry, vol 280, no. 17, 2005) using RNA interference. A lentivirus-delivered short-hairpin RNA (shRNA) was introduced in DM1 myoblasts and demonstrated to down regulate nuclear retained mutant DMPK mRNAs. Four shRNA molecules were tested, two were complementary against coding regions of DMPK, one against a unique sequence in the 3' UTR and one negative control with an irrelevant sequence. The first two shRNAs were capable of down regulating the mutant DMPK transcript with the amplified repeat to about 50%, but even more effective in down regulating the cytoplasmic wildtype transcript to about 30% or less. Equivalent synthetic siRNA delivered by cationic lipids was ineffective. The shRNA directed at the 3' UTR sequence proved to be ineffective for both transcripts. Hence, also this approach is not targeted selectively to the expanded repeat mRNA species.

(iii) A third approach by Furling et al. (Gene Therapy, Vol. 10, p 795-802, 2003) used a recombinant retrovirus expressing a 149-bp long antisense RNA to inhibit DMPK mRNA levels in human DM1 myoblasts. A retrovirus was designed to provide DM1 cells with the 149 bp long antisense RNA complementary to a 39 bp-long (CUG)13 repeat and a 110 bp region following the repeat to increase specificity. This method yielded a decrease in mutated (repeat expanded) DMPK transcript of 80%, compared to a 50% reduction in the wild type DMPK transcript and restoration of differentiation and functional characteristics in infected DM1 myoblasts. Hence, also this approach is not targeted selectively to the expanded repeat mRNA species, it depends on a very long antisense RNA and can only be used in combination with recombinant viral delivery techniques.

DETAILED DESCRIPTION OF THE INVENTION

The methods and techniques described above provide nucleid acid based methods that cause non-selective breakdown of both the affected repeat expanded allele and unaffected (normal) allele for genetic diseases that are associated with repeat instability and/or expansion. Moreover, the art employs sequences specific for the gene associated with the disease and does not provide a method that is applicable to several genetic disorders associated with repeat expansion. Finally, the art only teaches methods that involve use of recombinant DNA vector delivery systems, which need to be adapted for each oligonucleotide and target cell and which still need to be further optimised.

The current invention provides a solution for these problems by using a short single stranded nucleic acid molecule that comprises or consists of a sequence, which is complementary to the expanded repeat region only, i.e. it does not rely on hybridisation to unique sequences in exons or introns of the repeat containing gene. Furthermore, it is not essential that the employed nucleic acid (oligonucleotide) reduces transcripts by the RNAse H mediated breakdown mechanism.

Without wishing to be bound by theory, the current invention may cause a decrease in transcript levels by alterations in posttranscriptional processing and/or splicing of the premature RNA. A decrease in transcript levels via alternative splicing and/or postranscriptional processing is thought to result in transcripts lacking the overly expanded or instable (tri)nucleotide repeat, but still possessing functional activities. The reduction of aberrant transcripts by altered RNA processing and/or splicing may prevent accumulation and/or translation of aberrant, repeat expanded transcripts in cells.

Without wishing to be bound by theory the method of the current invention is also thought to provide specificity for the affected transcript with the expanded repeat because the kinetics for hybridisation to the expanded repeat are more favourable. The likelihood that a repeat specific complementary nucleic acid oligonucleotide molecule will hybridise to a complementary stretch in an RNA or DNA molecule increases with the size of the repetitive stretch. RNA molecules and in particular RNA molecules comprising repetitive sequences are normally internally paired, forming a secondary structure comprising open loops and closed hairpin parts. Only the open parts are relatively accessible for complementary nucleic acids. The short repeat stretches of a wild type transcript not associated with disease is often only 5 to about 20-40 repeats and due to the secondary structure relatively inaccessible for base pairing with a complementary nucleic acid. In contrast, the repeat units of the expanded repeat and disease associated allele is normally at least 2 fold expanded but usually even more, 3, 5, 10 fold, up to 100 or even more than 1000 fold expansion for some unstable repeat disorders. This expansion increases the likelihood that part of the repeat is, at least temporarily, in an open loop structure and thereby more accessible to base pairing with a complementary nucleic acid molecule, relative to the wild type allele. So despite the fact that the oligonucleotide is complementary to a repeat sequence present in both wildtype and repeat-expanded transcripts and could theoretically hybridise to both transcripts, the current invention teaches that oligonucleotides complementary to the repetitive tracts preferably hybridise to the disease-associated or disease-causing transcripts and leave the function of normal transcripts relatively unaffected. This selectivity is beneficial for treating diseases associated with repeat instability irrespective of the mechanism of reduction of the aberrant transcript.

The invention thus provides a method for the treatment of unstable cis-element DNA repeat associated genetic disorders, by providing nucleic acid molecules that are complementary to and/or capable of hybridising to the repetitive sequences only. This method thereby preferentially targets the expanded repeat transcripts and leaves the transcripts of the normal, wild type allele relatively unaffected. This is advantageous since the normal allele can thereby provide for the normal function of the gene, which is at least desirable and, depending on the particular gene with unstable DNA repeats, may in many cases be essential for the cell and/or individual to be treated.

Furthermore, this approach is not limited to a particular unstable DNA repeat associated genetic disorder, but may be applied to any of the known unstable DNA repeat diseases, such as, but not limited to: coding regions repeat diseases having a polyglutamine (CAG) repeat: Huntington's disease, Haw River syndrome, Kennedy's disease/spinobulbar muscular atrophy, spino-cerebellar ataxia, or diseases having polyalanine (GCG) repeats such as: infantile spasm syndrome, deidocranial dysplasia, blepharophimosis/ptosis/epicanthus invensus syndrome, hand-foot-genital syndrome, synpolydactyly, oculopharyngeal muscular dystrophy, holoprosencephaly. Diseases with repeats in non-coding regions of genes to be treated according to the invention comprise the trinucleotide repeat disorders (mostly CTG and/or CAG and/or CCTG repeats): myotonic dystrophy type 1, myotonic dystrophy type 2, Friedreich's ataxia (mainly GAA), spino-cerebellar ataxia, autism. Furthermore, the method of the invention can be applied to fragile site associated repeat disorder comprising various fragile X-syndromes, Jacobsen syndrome and other unstable repetitive element disorders such as myoclonus epilepsy, facioscapulohumeral dystrophy and certain forms of diabetes mellitus type 2.

Another advantage of the current invention is that the oligonucleotides specific for a repeat region may be administered directly to cells and it does not rely on vector-based delivery systems. The techniques described in the prior art, for instance those mentioned above for treatment of DM1 and removal of DMPK transcripts from cells, require the use of vector based delivery systems to administer sufficient levels of oligonucleotides to the cell. The use of plasmid or viral vectors is yet less desirable for therapeutic purposes because of current strict safety regulations for therapeutic recombinant DNA vectors, the production of sufficient recombinant vectors for broad clinical application and the limited control and reversibility of an exaggerated (or non-specific) response after application. Nevertheless, optimisation in future is likely in these areas and viral delivery of plasmids could yield an advantageous long lasting effect. The current inventors have surprisingly found that oligo-nucleotides that comprise or consist of a sequence that is complementary to repetitive sequences of expanded repeat transcripts, due to the expansion of their molecular target for hybridisation, have a much increased affinity and/or avidity for their target in comparison to oligonucleotides that are specific for unique sequences in a transcript. Because of this high affinity and avidity for the repeat expanded target transcript, lower amounts of oligonucleotide suffice to yield sufficient inhibition and/or reduction of the repeat expanded allele by RNase H degradation, RNA interference degradation or altered post-transcriptional processing (comprising but not limited to splicing or exon skipping) activities. The oligonucleotides of the current invention which are complementary to repetitive sequences only, may be produced synthetically and are potent enough to be effective when delivered directly to cells using commonly applied techniques for direct delivery of oligonucleotides to cells and/or tissues. Recombinant vector delivery systems may, when desired, be circumvented by using the method and the oligonucleotide molecules of the current invention.

In a first aspect, the current invention discloses and teaches the use of an oligonucleotide comprising or consisting of a sequence that is complementary only to a repetitive sequence in a human gene transcript for the manufacture of a medicament for the diagnosis, treatment or prevention of a cis-element repeat instability associated genetic disorders in humans. The invention hence provides a method of treatment for cis-element repeat instability associated genetic disorders.

In a second aspect, the invention also pertains to an oligonucleotide which can be used in the first aspect of the invention and/or applied in method of the invention to prevent the accumulation and/or translation of repeat expanded transcripts in cells.

An oligonucleotide of the invention may comprise a sequence that is complementary only to a repetitive sequence as defined below. Preferably, the repetitive sequence is at least 50% of the length of the oligonucleotide of the invention, more preferably at least 60%, even more preferably at least 70%, even more preferably at least 80%, even more preferably at least 90% or more. In a most preferred embodiment, the oligonucleotide of the invention consists of a sequence that is complementary only to a repetitive sequence as defined below. For example, an oligonucleotide may comprise a sequence that is complementary only to a repetitive sequence as defined below and a targeting part, which is later on called a targeting ligand.

A repeat or repetitive element or repetitive sequence or repetitive stretch is herein defined as a repetition of at least 3, 4, 5, 10, 100, 1000 or more, of a repetitive unit or repetitive nucleotide unit or repeat nucleotide unit comprising a trinucleotide repetitive unit, or alternatively a 4, 5 or 6 nucleotide repetitive unit, in a transcribed gene sequence in the genome of a subject, including a human subject.

An oligonucleotide may be single stranded or double stranded. Double stranded means that the oligonucleotide is an heterodimer made of two complementary strands, such as in a siRNA. In a preferred embodiment, an oligonucleotide is single stranded. A single stranded oligonucleotide has several advantages compared to a double stranded siRNA oligonucleotide: (i) its synthesis is expected to be easier than two complementary siRNA strands; (ii) there is a wider range of chemical modifications possible to optimise more effective uptake in cells, a better (physiological) stability and to decrease potential generic adverse effects; and (iii) siRNAs have a higher potential for non-specific effects and exaggerated pharmacology (e.g. less control possible of effectiveness and selectivity by treatment schedule or dose) and (iv) siRNAs are less likely to act in the nucleus and cannot be directed against introns. Therefore, in a preferred embodiment of the first aspect, the invention relates to the use of a single stranded oligonucleotide comprising or consisting of a sequence that is complementary only to a repetitive sequence in a human gene transcript for the manufacture of a medicament for the diagnosis, treatment or prevention of a cis-element repeat instability associated genetic disorders in humans.

The oligonucleotide(s) preferably comprise at least 10 to about 50 consecutive nucleotides complementary to a repetitive element, more preferably 12 to 45 nucleotides, even more preferably 12 to 30, and most preferably 12 to 25 nucleotides complementary to a repetitive stretch, preferably having a trinucleotide repeat unit or a tetranucleotide repeat unit. The oligonucleotide may be complementary to and/or capable of hybridizing to a repetitive stretch in a coding region of a transcript, preferably a polyglutamine (CAG) or a polyalanine (GCG) coding tract. The oligonucleotide may also be complementary to and/or capable of hybridizing to a non-coding region for instance 5' or 3' untranslated regions, or intronic sequences present in precursor RNA molecules.

In a preferred embodiment the oligonucleotide to be used in the method of the invention comprises or consists of a sequence that is complementary to a repetitive element having as repetitive nucleotide unit a repetitive nucleotide unit selected from the group consisting of (CAG)n (SEQ ID NO:18), (GCG)n (SEQ ID NO:19), (CUG)n (SEQ ID NO:20), (CGG)n (SEQ ID NO:21) (GAA)n (SEQ ID NO:35), (GCC)n (SEQ ID NO:36) and (CCUG)n (SEQ ID NO:22) and said oligonucleotide being a single or double stranded oligonucleotide. Preferably, the oligonucleotide is double stranded.

The use of an oligonucleotide that comprises or consists of a sequence that is complementary to a polyglutamine (CAG)n tract in a transcript is particularly useful for the diagnosis, treatment and/or prevention of the human disorders Huntington's disease, several forms of spino-cerebellar ataxia or Haw River syndrome, X-linked spinal and bulbar muscular atrophy and/or dentatorubral-pallidoluysian atrophy caused by repeat expansions in the HD, HDL2/JPH3, SBMA/AR, SCA1/ATX1, SCA2/ATX2, SCA3/ATX3, SCA6/CACNAIA, SCAT, SCA17, AR or DRPLA human genes.

The use of an oligonucleotide that comprises or consists of a sequence that is complementary to a polyalanine (GCG)n tract in a transcript is particularly useful for the diagnosis, treatment and/or prevention of the human disorders: infantile spasm syndrome, deidocranial dysplasia, blepharophimosis, hand-foot-genital disease, synpolydactyly, oculopharyngeal muscular dystrophy and/or holoprosencephaly, which are caused by repeat expansions in the ARX, CBFA1, FOXL2, HOXA13, HOXD13, OPDM/PABP2, TCFBR1 or ZIC2 human genes.

The use of an oligonucleotide that comprises or consists of a sequence that is complementary to a (CUG)n repeat in a transcript and is particularly useful for the diagnosis, treatment and/or prevention of the human genetic disorder myotonic dystrophy type 1, spino-cerebrellar ataxia 8 and/or Huntington's disease-like 2 caused by repeat expansions in the DM1/DMPK, SCA8 or JPH3 genes respectively. Preferably, these genes are from human origin.

The use of an oligonucleotide that comprises or consists of a sequence that is complementary to a (CCUG)n repeat in a transcript is particularly useful for the diagnosis, treatment and/or prevention of the human genetic disorder myotonic dystrophy type 2, caused by repeat expansions in the DM2/ZNF9 gene.

The use of an oligonucleotide that comprises or consists of a sequence that is complementary to a (CGG)n repeat in a transcript is particularly useful for the diagnosis, treatment and/or prevention of human fragile X syndromes, caused by repeat expansion in the FRAXA/FMR1, FRAXE/FMR2 and FRAXF/FAM11A genes.

The use of an oligonucleotide that comprises or consists of a sequence that is complementary to a (CCG)n repeat in a transcript is particularly useful for the diagnosis, treatment and/or prevention of the human genetic disorder Jacobsen syndrome, caused by repeat expansion in the FRA11B/CBL2 gene.

The use of an oligonucleotide that comprises or consists of a sequence that is complementary to a (GAA)n repeat in a transcript is particularly useful for the diagnosis, treatment and/or prevention of the human genetic disorder Friedreich's ataxia.

The use of an oligonucleotide that comprises or consists of a sequence that is complementary to a (ATTCT)n repeat in an intron is particularly useful for the diagnosis, treatment and/or prevention of the human genetic disorder Spinocerebellar ataxia type 10 (SCA10).

The repeat-complementary oligonucleotide to be used in the method of the invention may comprise or consist of RNA, DNA, Locked nucleic acid (LNA), peptide nucleic acid (PNA), morpholino phosphorodiamidates (PMO), ethylene bridged nucleic acid (ENA) or mixtures/hybrids thereof that comprise combinations of naturally occurring DNA and RNA nucleotides and synthetic, modified nucleotides. In such oligonucleotides, the phosphodiester backbone chemistry may further be replaced by other modifications, such as phosphorothioates or methylphosphonates. Other oligonucleotide modifications exist and new ones are likely to be developed and used in practice. However, all such oligonucleotides have the character of an oligomer with the ability of sequence specific binding to RNA. Therefore in a preferred embodiment, the oligonucleotide comprises or consists of RNA nucleotides, DNA nucleotides, locked nucleic acid (LNA) nucleotides, peptide nucleic acid (PNA) nucleotides, morpholino phosphorodiamidates, ethylene-bridged nucleic acid (ENA) nucleotides or mixtures thereof with or without phosphorothioate containing backbones.

Oligonucleotides containing at least in part naturally occurring DNA nucleotides are useful for inducing degradation of DNA-RNA hybrid molecules in the cell by RNase H activity (EC.3.1.26.4).

Naturally occurring RNA ribonucleotides or RNA-like synthetic ribonucleotides comprising oligonucleotides may be applied in the method of the invention to form double stranded RNA-RNA hybrids that act as enzyme-dependent antisense through the RNA interference or silencing (RNAi/siRNA) pathways, involving target RNA recognition through sense-antisense strand pairing followed by target RNA degradation by the RNA-induced silencing complex (RISC).

Alternatively or in addition, steric blocking antisense oligonucleotides (RNase-H independent antisense) interfere with gene expression or other precursor RNA or messenger RNA-dependent cellular processes, in particular but not limited to RNA splicing and exon skipping, by binding to a target sequence of RNA transcript and getting in the way of processes such as translation or blocking of splice donor or splice acceptor sites. Alteration of splicing and exon skipping techniques using modified antisense oligonucleotides are well documented, known to the skilled artisan and may for instance be found in U.S. Pat. No. 6,210,892, WO9426887, WO04/083446 and WO02/24906. Moreover, steric hindrance may inhibit the binding of proteins, nuclear factors and others and thereby contribute to the decrease in nuclear accumulation or ribonuclear foci in diseases like DM1.

The oligonucleotides of the invention, which may comprise synthetic or modified nucleotides, complementary to (expanded) repetitive sequences are useful for the method of the invention for reducing or inactivating repeat containing transcripts via the siRNA/RNA interference or silencing pathway.

Single or double stranded oligonucleotides to be used in the method of the invention may comprise or consist of DNA nucleotides, RNA nucleotides, 2'-O substituted ribonucleotides, including alkyl and methoxy ethyl substitutions, peptide nucleic acid (PNA), locked nucleic acid (LNA) and morpholino (PMO) antisense oligonucleotides and ethylene-bridged nucleotides (ENA) and combinations thereof, optionally chimeras with RNAse H dependent antisense. Integration of locked nucleic acids in the oligonucleotide changes the conformation of the helix after base pairing and increases the stability of the duplex. Integration of LNA bases into the oligonucleotide sequence can therefore be used to increase the ability of complementary oligonucleotides of the invention to be active in vitro and in vivo to increase RNA degradation inhibit accumulation of transcripts or increase exon skipping capabilities. Peptide nucleic acids (PNAs), an artificial DNA/RNA analog, in which the backbone is a pseudopeptide rather than a sugar, have the ability to form extremely stable complexes with complementary DNA oligomers, by increased binding and a higher melting temperature. Also PNAs are superior reagents in antisense and exon skipping applications of the invention. Most preferably, the oligonucleotides to be used in the method of this invention comprise, at least in part or fully, 2'-O-methoxy ethyl phosphorothioate RNA nucleotides or 2'-O-methyl phosphorothioate RNA nucleotides. Oligonucleotides comprising or consisting of a sequence that is complementary to a repetitive sequence selected from the group consisting of (CAG)n, (GCG)n, (CUG)n, (CGG)n, (CCG)n, (GAA)n, (GCC)n and (CCUG)n having a length of 10 to 50, more preferably 12 to 35, most preferably 12 to 25 nucleotides, and comprising 2'-O-methoxyethyl phosphorothioate RNA nucleotides, 2'-O-methyl phosphorothioate RNA nucleotides, LNA nucleotides or PMO nucleotides are most preferred for use in the invention for the diagnosis, treatment of prevention of cis-element repeat instability genetic disorders.

Accordingly, in a preferred embodiment, an oligonucleotide of the invention and used in the invention comprises or consists of a sequence that is complementary to a repetitive sequence selected from the group consisting of (CAG)n, (GCG)n, (CUG)n, (CGG)n, (GAA)n, (GCC)n and (CCUG)n, has a length of 10 to 50 nucleotides and is further characterized by:
   a) comprising 2'-O-substituted RNA phosphorothioate nucleotides such as 2'-O-methyl or 2'-O-methoxy ethyl RNA phosphorothiote nucleotides, LNA nucleotides or PMO nucleotides. The nucleotides could be used in any combination and/or with DNA phosphorothioate or RNA nucleotides; and/or
   b) being a single stranded oligonucleotide.

Accordingly, in another preferred embodiment, an oligonucleotide of the invention and used in the invention comprises or consists of a sequence that is complementary to a repetitive sequence selected from the group consisting of (CAG)n, (GCG)n, (CUG)n, (CGG)n, (GAA)n, (GCC)n and (CCUG)n, has a length of 10 to 50 nucleotides and is further characterized by:
   c) comprising 2'-O-substituted RNA phosphorothioate nucleotides such as 2'-O-methyl or 2'-O-methoxy ethyl RNA phosphorothiote nucleotides, LNA nucleotides or PMO nucleotides. The nucleotides could be used in combination and/or with DNA phosphorothioate or RNA nucleotides; and/or
   d) being a double stranded oligonucleotide.

In case, the invention relates to a double stranded oligonucleotide with two complementary strands, the antisense strand, complementary only to a repetitive sequence in a human gene transcript, this double stranded oligonucleotide is preferably not the siRNA with antisense RNA strand $(CUG)_7$ and sense RNA strand $(GCA)_7$ applied to cultured monkey fibroblast (COS-7) or human neuroblastoma (SH-SY5Y) cell lines with or without transfection with a human Huntington gene exon 1 fused to GFP and as depicted in Wanzhao Liu et al (Wanzhao Liu et al, (2003), Proc. Japan Acad, 79: 293-298). More preferably, the invention does neither relate to the double stranded oligonucleotide siRNA (with antisense strand $(CUG)_7$ and sense strand $(GCA)_7$) nor to its use for the manufacture of a medicament for the treatment or prevention of Huntington disease, even more preferably for the treatment or prevention of Huntington disease gene exon 1 containing construct.

Although use of a single oligonucleotide may be sufficient for reducing the amount of repeat expanded transcripts, such as nuclear accumulated DMPK or ZNF9 transcripts or segments thereof or sufficient reduction of accumulation of repeat expanded HD protein, it is also within the scope of the invention to combine 2, 3, 4, 5 or more oligonucleotides. The oligonucleotide comprising or consisting of a sequence that is complementary to a repetitive part of a transcript may be advantageously combined with oligonucleotides that comprise or consist of sequences that are complementary to and/or capable of hybridizing with unique sequences in a repeat containing transcript. The method of the invention and the medicaments of the invention comprising repeat specific oligonucleotides may also be combined with any other treatment or medicament for cis-element repeat instability genetic disorders. For diagnostic purposes the oligonucleotide used in the method of the invention may be provided with a radioactive label or fluorescent label allowing detection of transcripts in samples, in cells in situ in vivo, ex vivo or in vitro. For myotonic dystrophy, labelled oligonucleotides may be used for diagnostic purposes, for visualisation of nuclear aggregates of DMPK or ZNF9 RNA transcript molecules with associated proteins. Fluorescent labels may comprise Cy3, Cy5, FITC, TRITC, Rhodamine, GFP and the like. Radioactive labels may comprise $^3H$, $^{35}S$, $^{32/33}P$, $^{125}I$. Enzymes and/or immunogenic haptens such as digoxigenin, biotin and other molecular tags (HA, Myc, FLAG, VSV, lexA) may also be used. Accordingly, in a further aspect, the invention discloses an vitro or ex vivo detection and/or diagnostic method wherein a oligonucleotide as defined above is used.

The oligonucleotides for use according to the invention are suitable for direct administration to cells, tissues and/or organs in vivo of individuals affected by or at risk of developing a cis-element repeat instability disorder, and may be administered directly in vivo, ex vivo or in vitro. Alternatively, the oligonucleotides may be provided by a nucleic acid vector capable of conferring expression of the oligonucleotide in human cells, in order to allow a sustainable source of the oligonucleotides. Oligonucleotide molecules according to the invention may be provided to a cell, tissue, organ and/or subject to be treated in the form of an expression vector that is capable of conferring expression of the oligonucleotide in human cells. The vector is preferably introduced in the cell by a gene delivery vehicle. Preferred vehicles for delivery are viral vectors such as retroviral vectors, adeno-associated virus vectors (AAV), adenoviral vectors, Semliki Forest virus vectors (SFV), EBV vectors and the like. Also plasmids, artificial chromosomes, plasmids suitable for targeted homologous recombination and integration in the human genome of cells may be suitably applied for delivery of oligonucleotides. Preferred for the current invention are those vectors wherein transcription is driven from polIII promoters, and/or wherein transcripts are in the form fusions with U1 or U7 transcripts, which yield good results for delivering small transcripts.

In a preferred embodiment, a concentration of oligonucleotide, which is ranged between about 0.1 nM and about 1 µM is used. More preferably, the concentration used is ranged between about 0.3 to about 400 nM, even more preferably between about 1 to about 200 nM. If several oligonucleotides are used, this concentration may refer to the total concentration of oligonucleotides or the concentration of each oligonucleotide added. The ranges of concentration of oligonucleotide(s) as given above are preferred concentrations for in vitro or ex vivo uses. The skilled person will understand that depending on the oligonucleotide(s) used, the target cell to be treated, the gene target and its expression levels, the medium used and the transfection and incubation conditions, the concentration of oligonucleotide(s) used may further vary and may need to be optimised any further.

More preferably, the oligonucleotides to be used in the invention to prevent, treat or diagnose cis-element repeat instability disorders are synthetically produced and administered directly to cells, tissues, organs and/or patients in formulated form in pharmaceutically acceptable compositions. The delivery of the pharmaceutical compositions to the subject is preferably carried out by one or more parenteral injections, e.g. intravenous and/or subcutaneous and/or intramuscular and/or intrathecal and/or intraventricular administrations, preferably injections, at one or at multiple sites in the human body. An intrathecal or intraventricular administration (in the cerebrospinal fluid) is preferably realized by introducing a diffusion pump into the body of a subject. Several diffusion pumps are known to the skilled person.

Pharmaceutical compositions that are to be used to target the oligonucleotide molecules comprising or consisting of a sequence that is complementary to repetitive sequences may comprise various excipients such as diluents, fillers, preservatives, solubilisers and the like, which may for instance be found in Remington: The Science and Practice of Pharmacy, 20th Edition. Baltimore, Md.: Lippincott Williams & Wilkins, 2000.

Particularly preferred for the method of the invention is the use of excipients that will aid in delivery of the oligonucleotides to the cells and into the cells, in particular excipients capable of forming complexes, vesicles and/or liposomes that deliver substances and/or oligonucleotide(s) complexed or trapped in the vesicles or liposomes through a cell membrane. Many of these substances are known in the art. Suitable substances comprise polyethylenimine (PEI), ExGen 500, synthetic amphiphils (SAINT-18), Lipofectin™, DOTAP and/or viral capsid proteins that are capable of self assembly into particles that can deliver oligonucleotides to cells. Lipofectin represents an example of liposomal transfection agents. It consists of two lipid components, a cationic lipid N-[1-(2,3 dioleoyloxy)propyl]-N,N, N-trimethylammonium chloride (DOTMA) (cp. DOTAP which is the methylsulfate salt) and a neutral lipid dioleoyl-phosphatidylethanolamine (DOPE). The neutral component mediates the intracellular release. Another group of delivery systems are polymeric nanoparticles. Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver oligonucleotides across cell membranes into cells. In addition to these common nanoparticle materials, the cationic peptide protamine offers an alternative approach to formulate oligonucleotides as colloids. This colloidal nanoparticle system can form so called proticles, which can be prepared by a simple self-assembly process to package and mediate intracellular release of the oligonucleotides. The skilled person may select and adapt any of the above or other commercially available alternative excipients and delivery systems to package and deliver oligonucleotides for use in the current invention to deliver oligonucleotides for the treatment of cis-element repeat instability disorders in humans.

In addition, the oligonucleotide could be covalently or non-covalently linked to a targeting ligand specifically designed to facilitate the uptake in to the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes. Such targeting ligand would also encompass molecules facilitating the uptake of oligonucleotides into the brain through the blood brain barrier. Therefore, in a preferred embodiment, an oligonucleotide in a medicament is provided with at least an excipient and/or a targeting ligand for delivery and/or a delivery device of the oligonucleotide to cells and/or enhancing its intracellular delivery. Accordingly, the invention also encompasses a pharmaceutically acceptable composition comprising an oligonucleotide of the invention and further comprising at least one excipient and/or a targeting ligand for delivery and/or a delivery device of the oligonucleotide to the cell and/or enhancing its intracellular delivery.

The invention also pertains to a method for the reduction of repeat containing gene transcripts in a cell comprising the administration of a single strand or double stranded oligonucleotide molecule, preferably comprising 2'-O-substituted RNA phosphorothioate nucleotides such as 2'-O-methyl or 2'-O-methoxy ethyl RNA phosphorothioate nucleotides or LNA nucleotides or PMO nucleotides, and having a length of 10 to 50 nucleotides that are complementary to the repetitive sequence only. The nucleotides could be used in combination and/or with DNA phosphorothioate nucleotides.

In this document and in its claims, the verb "to comprise" and its conjugations is used in its non-limiting sense to mean that items following the word are included, but combinations and/or items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

FIGURE LEGENDS

FIG. 1: Northern blot of RNA isolated from myotubes transfected with different oligonucleotides or mock control. The myotubes were derived from immorto mouse myoblast cell lines containing a transgenic human DMPK genes with (CTG)n repeat expansion length of approximately 500 next to its normal mouse DMPK gene without (CTG) repeat. The blot shows human DMPK mRNA (top), mouse DMPK (mDMPK) mRNA (middle) and mouse GAPDH mRNA (bottom).

Figure 2:
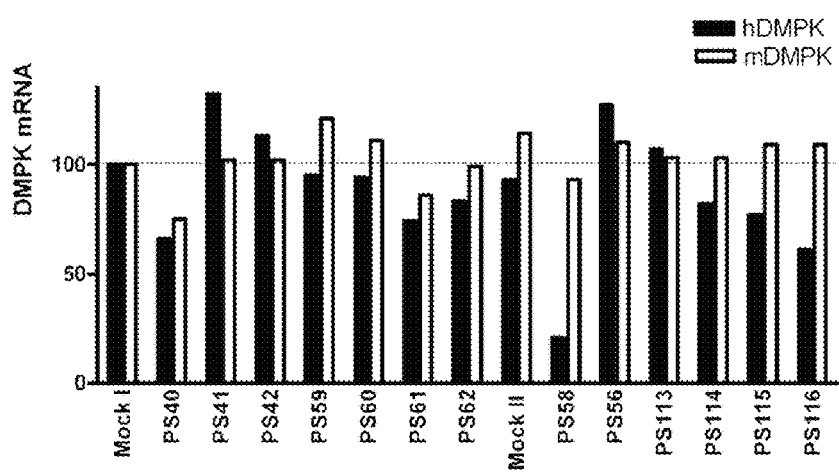

FIG. 2: The human and mouse DMPK signals of FIG. 1 were quantified by phosphoimager analysis and normalized to the GAPDH signal. The results are expressed relative to the mock treatment (set to 100).

Figure 3:
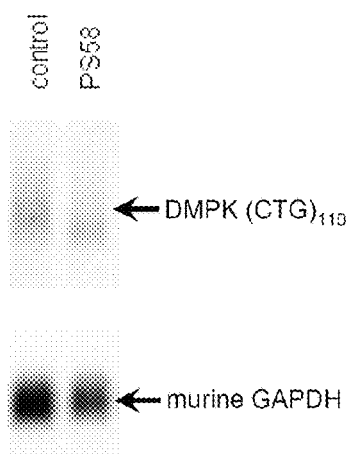

FIG. 3: Northern blot of total RNA isolated from murine myotubes containing a mouse-human chimaeric DMPK gene in which the 3' part of the mDMPK gene was replaced by the cognate segment of the human DMPK gene including a $(CTG)_{110}$-repeat. The blot was probed for DMPK mRNA (upper panel) and mouse GAPDH mRNA (bottom). Cells were transfected with antisense oligonucleotide PS58 or control.

Figure 4:
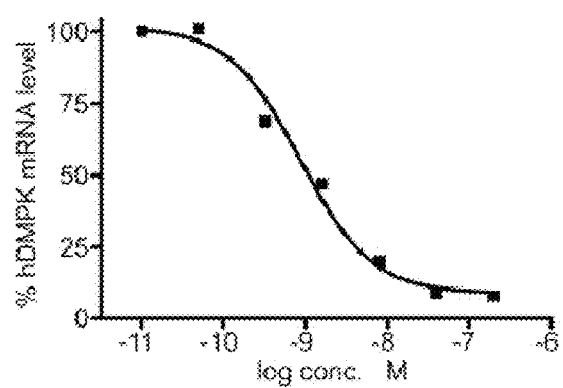

FIG. 4 shows the response of DM500 myotubes treated with various concentrations of oligonucleotide PS58. The expression of hDMPK was quantified via Northern blot analysis followed by phosphoimager analysis. The signal was normalised to the GAPDH signal and expressed relative to the response after mock treatment.

Figure 5:
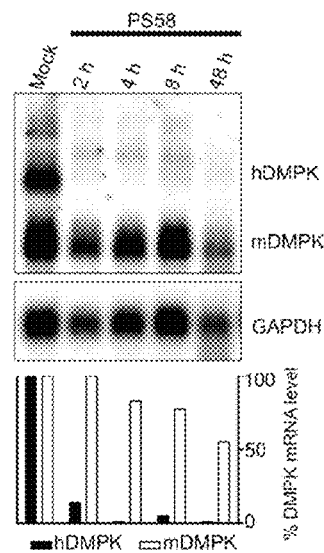

FIG. 5 shows the Northern blot of total RNA of DM500 myotubes transfected with 200 nM PS58 at different time points: 2 h, 4 h, 8 h and 48 h before harvesting. Mock treatment was performed 48 h before harvesting. Northern blots show human and mouse DMPK and mouse GAPDH mRNA. These were quantified by phosphoimager and the normalized DMPK signal was expressed relative to mock treatment.

Figure 6:
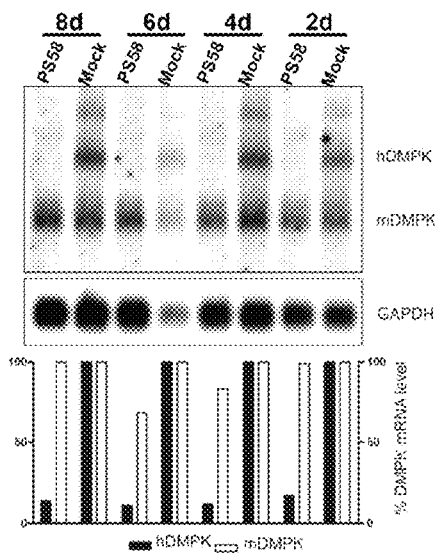

FIG. 6 shows the Northern blot of total RNA of DM500 myotubes harvested 2 d, 4 d, 6 d and 8 d after transfection with 200 nM PS58 or mock control. Northern blot analysis and quantification was performed as before.

Figure 7:
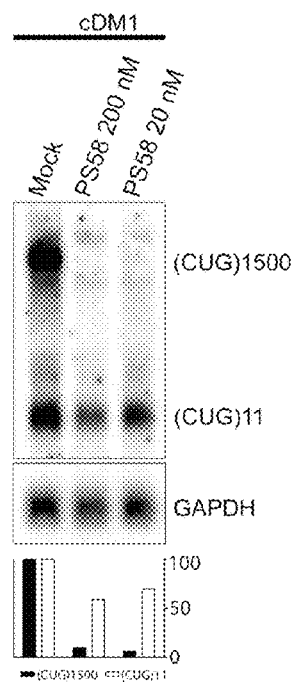

FIG. 7 shows a Northern blot of total RNA from MyoD-transformed myoblasts treated with oligonucleotide PS58 (20 and 200 nM) or mock control. The myoblasts were derived from fibroblasts obtained from a congenital myotonic dystrophy type I patient bearing a hDMPK allele with a triplet repeat expansion length of approximately 1500 and a hDMPK allele with normal length of 11 repeats. The Northern blot was hybridized with a human DMPK (hDMPK) probe and GAPDH mRNA probe. The human DMPK signals were normalized to the GAPDH signal and expressed relative to mock control.

Figure 8:
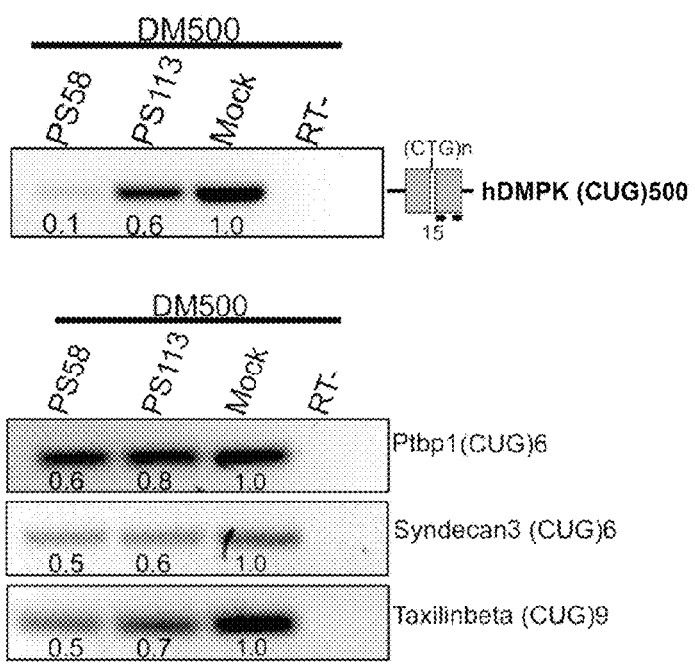

FIG. 8 shows the RT-PCR analysis of DM500 myotubes transfected with 200 nM of oligonucleotide PS58, specific to the (CUG) repeat sequence only, oligonucleotide PS113, specific to a sequence in exon 1, or mock control. RT-PCR analysis was performed with primers specific for hDMPK mRNA and three other gene transcripts with a naturally occurring (CUG) repeat in mice: Ptbp1 mRNA with a (CUG)6, Syndecan3 mRNA with a (CUG)6 and Taxilinbeta mRNA with a (CUG)9. The intensity of the signals were normalized to the actin signal and expressed relative to mock control.

Figure 9:
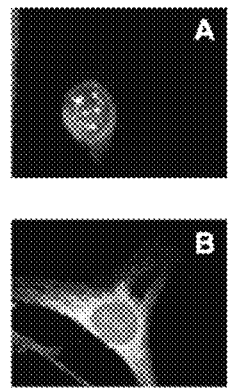

FIG. 9 shows FISH analysis of DM500 myoblasts transfected with 200 nM PS58 (B) or mock control (A). Forty eight hours after the start of the treatment, the cells were washed and fixed and subsequently hybridized with fluorescently labeled oligonucleotide Cy3-(CAG)10-Cy3. The ribonuclear foci indicative of hDMPK (CUG)$_{500}$ mRNA aggregation in the nucleus were visualized using a Bio-Rad MRC1024 confocal laser scanning microscope and LaserSharp2000 acquisition software.

Figure 10:
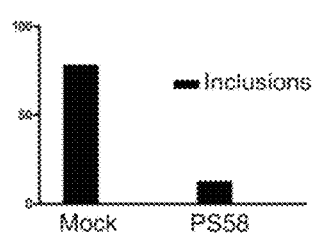

FIG. 10 shows the relative cell count for the presence of ribonuclear foci in the nucleus of DM500 myoblasts transfected with PS58 or mock control from the experiment depicted in FIG. 9.

Figure 11:
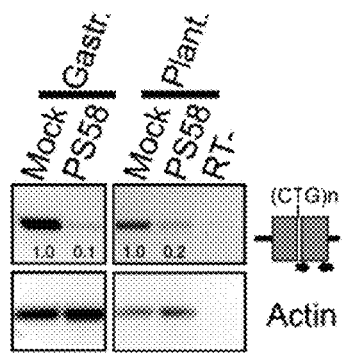

FIG. 11 shows the RT-PCR analysis of hDMPK mRNA in muscle of DM500 mice treated with PS58 or mock control. Shortly, PS58 (2 nmol) was injected in the GPS complex of one-year-old DM500 mice and this procedure was repeated after 24 h. After 15 days, *M. plantaris* and *M. gastrocnemius* were isolated and RT-PCR was performed on total RNA for hDMPK and mouse actin. The intensity of the hDMPK signal was normalized to the actin signal and the values expressed relative to mock control.

Figure 12:
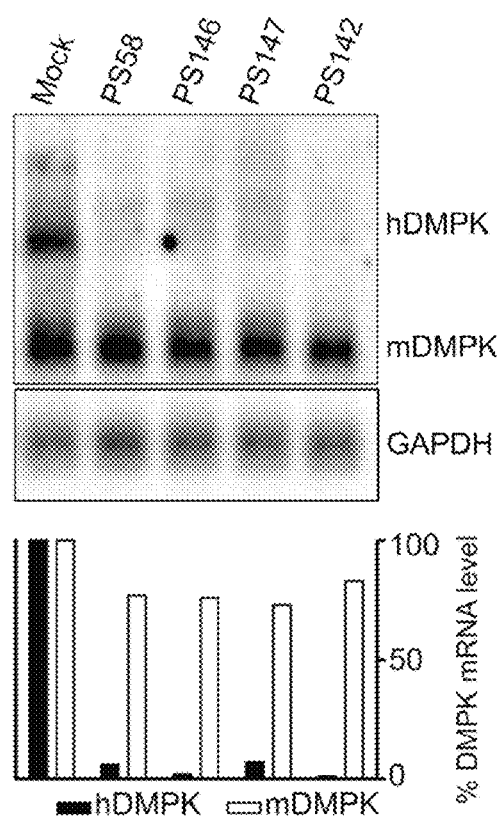

FIG. 12 shows a Northern blot analysis of DM500 myotubes treated with different oligonucleotides (200 nM) or mock control. PS58 (SEQ ID NO:6), PS146 (SEQ ID NO:16) and PS147 (SEQ ID NO:17 carried a full 2'-O-methyl phosphorothiate backbone, but differed in length, (CAG)7, (CUG)10 and (CUG)5, respectively. PS142 has a complete phosphorothiate DNA backbone with a (CAG)7 sequence (SEQ ID NO:15). hDMPK and mDMPK signals were normalized to mouse GAPDH and expressed as percentage to mock control. Quantification is shown in the lower panel.

EXAMPLES

Example 1

Immortomyoblast cell lines were derived from DM500 or CTG110 mice using standard techniques known to the skilled person. DM500 mice were derived from mice obtained from de Gourdon group in Paris. CTG110 mice are described below and present at the group of Wieringa and Wansink in Nijmegen. Immortomyoblast cell lines DM500 or CTG110 with variable (CTG)n repeat length in the DMPK gene were grown subconfluent and maintained in a 5% $CO_2$ atmosphere at 33° C. on 0.1% gelatin coated dishes. Myoblast cells were grown subconfluent in DMEM supplemented with 20% FCS, 50 µg/ml gentamycin and 20 units of γ-interferon/ml. Myotube formation was induced by growing myoblast cells on Matrigel (BD Biosciences) coated dishes and placing a confluent myoblast culture at 37° C. and in DMEM supplemented with 5% horse serum and 50 µg/ml gentamycin. After five days on this low serum media contracting myotubes arose in culture and were transfected with the desired oligonucleotides. For transfection NaCl (500 mM, filter sterile), oligonucleotide and transfection reagens PEI (ExGen 500, Fermentas) were added in this specific order and directly mixed. The oligonucleotide transfection solution contained a ratio of 5 µl ExGen500 per ug oligonucleotide which is according to the instructions (ExGen 500, Fermentas). After 15 minutes of incubation at room temperature the oligonucleotide transfection solution was added to the low serum medium with the cultured myotubes and gently mixed. The final oligonucleotide concentration was 200 nM. Mock control treatment is carried out with transfection solution without an oligonucleotide. After four hours of incubation at 37° C., fresh medium was added to the culture (resulting in a dilution of approximately 2.3×) and incubation was extended overnight at 37° C. The next day the medium containing the oligonucleotide was removed and fresh low serum medium was added to the myotubes which were kept in culture at 37° C. for another day. Forty eight hours after the addition of oligonucleotide to the myotube culture (which is seven days after switching to low serum conditions to induced myotube formation), RNA was isolated with the "Total RNA mini kit" (Bio-Rad) and prepared for Northern blot and RT-PCR analysis. The Northern blot was hybridized with a radioactive human DMPK (hDMPK) probe and a mouse GAPDH probe. The probe used for DMPK is a human DMPK cDNA consisting of the DMPK open reading frame with full 3' UTR and 11 CTGs.

The human and mouse DMPK signal were quantified by phosphoimager analysis and normalized to the GAPDH signal. Primers that were used for the RT-PCR for hDMPK mRNA were situated in the 3' untranslated part with the sequence 5'-GGGGGATCACAGACCATT-3' (SEQ ID NO:23) and 5'-TCAATGCATCCAAAACGTGGA-3' (SEQ ID NO:24) and for murine actin the primers were as followed: Actin sense 5'-GCTAYGAGCTGCCTGACGG-3' (SEQ ID NO:25) and Actin antisense 5'-GAGGCCAG-GATGGAGCC-3' (SEQ ID NO:26). PCR products were run on an agarose gel and the signal was quantified using Labworks 4.0 (UVP Biolmaging systems, Cambridge, United Kingdom). The intensity of each band was normalized to the intensity of the corresponding actin band and expressed relative to mock control.

Thirteen different oligonucleotides were tested (for an overview see Table 1) as described above on the immortomyoblast DM500 cell line containing transgenic human DMPK gene with (CTG)n repeat length of approximately 500 and a normal mouse DMPK gene without (CTG) repeat. FIG. 1 shows the Northern blot of the isolated RNA from the oligonucleotide transfected myotubes visualized with the hDMPK probe and a GAPDH probe for loading control. Quantification of the human DMPK (with CTG repeat) and murine DMPK (without CTG repeat) signal on the Northern blot is shown in FIG. 2. The signal was normalized to murine GAPDH and expressed relative to mock control.

Table 2 indicates the level of hDMPK mRNA reduction that is caused by a specific oligonucleotide. The minus (−) stands for no reduction and the number of positive signs (+) stands for the relative level of hDMPK mRNA break-down. Clearly, oligonucleotide PS58, specifically targeted to the repeat sequence, is much more potent in reducing or altering hDMPK transcripts than the other oligonucleotides complementary to unique sequences in the hDMPK transcripts.

FIG. 3 shows the effect of PS58 in murine immortomyotubes derived from CTG110 mice, a knock-in mouse containing a DMPK gene with the 3' part of the human DMPK gene including a (CTG) repeat of approximately 110. Northern blot analysis showed that the DMPK transcript containing the (CTG)110 repeat was reduced by the treatment with oligonucleotide PS58 but not after mock treatment.

Example 2 (FIG. 4)

The DM500 immortomyoblast cell line carrying a human DMPK gene with an approximate (CTG)500 repeat expansion was cultured, prepared and transfected as described above (see example 1). In this example, the transfection was carried out with PS58 at different concentrations. Eighty four hours after start of treatment, the myotubes were harvested and Northern blot analysis was performed on isolated RNA as described above (see example 1).

FIG. 4 shows the quantification of the hDMPK mRNA signal preformed by phosphoimager analysis and normalized to the GAPDH signal at different concentrations. Under these conditions, a half maximal effect was observed at around 1 nM.

Example 3 (FIGS. 5 and 6)

The DM500 immortomyoblast cell line carrying a human DMPK gene with an approximate (CTG)500 repeat expansion was cultured, prepared and transfected as described above (see example 1). However, in this example the transfection with 200 nM PS58 was carried out at different time points. Usually DM500 myotubes were harvested seven days after switching to low serum conditions to induce myotube formation. The standard procedure (as in example 1 and 2) was to start treatment (transfection) 48 h (two days) before harvesting. Now, treatment with PS58 was started 2 h-48 h (FIG. 5) or 2 d-8 d (FIG. 6) before harvesting. Northern blot analysis and quantification was performed as before.

FIG. 5 shows that expanded hDMPK mRNA in DM500 myotubes was decreased rapidly within 2 h of treatment with oligonucleotide PS58 compared to mock control treatment.

FIG. 6 shows a persistent decrease in expanded hDMPK mRNA in DM500 myotubes for at least 8 days. Please note that in the case of the 8 d experiment, cells were transfected in the myoblast stage (approximately 60% confluent, 33° C., high serum) and that they have received fresh medium on various occasions until harvesting (including a change to low serum at 37° C., two days after transfection). Example 2 and 3 are indicative of a highly efficient inhibitory intervention by an oligonucleotide directed solely to the repeat expansion. The magnitude of this effect might be influenced by the relative low levels of hDMPK expression in these model cell systems, which normally is also seen in humans.

Example 4 (FIG. 7)

In this example, fibroblasts obtained from a human patient with congenital myotonic dystrophy type 1 (cDM1) were used. These patient cells carry one disease causing DMPK allele with a triplet repeat expansion length of 1500 and one normal DMPK allele with a repeat length of 11. The size of the (CTG)n expansion on both alleles was confirmed with PCR and Southern blotting.

The fibroblasts were grown subconfluent and maintained in a 5% $CO_2$ atmosphere at 37° C. on 0.1% gelatin coated dishes. Fibroblasts were grown subconfluent in DMEM supplemented with 10% FCS and 50 µg/ml gentamycin. Myotube formation was induced by growing fibroblasts cells on Matrigel (BD Biosciences) coated dishes and infecting the cells at 75% confluency with MyoD-expressing adenovirus (Ad5Fib50MyoD, Crucell, Leiden) (MOI=100) in DMEM supplemented with 2% HS and 50 µg/ml gentamycin for 2 hours. After the incubation period MyoD adenovirus was removed and DMEM supplemented with 10% FCS and 50 µg/ml gentamycin was added. The cells were maintained in this medium in a 5% $CO_2$ atmosphere at 37° C. until 100% confluency. At this point cells were placed in DMEM supplemented with 2% FCS and 50 µg/ml gentamycin. After five days on this low serum media cells were transfected with PS58 following the procedure according to the instructions (ExGen 500, Fermentas) and as described above. The final oligonucleotide concentration was 200 nM and 20 nM. Fourty eight hours after start of the treatment (which is seven days after switching to low serum conditions), RNA was isolated with the "Total RNA mini kit" (Bio-Rad) and prepared for Northern blot. The Northern blot was hybridized with a radioactive human DMPK (hDMPK) and mouse GAPDH mRNA probe. The human DMPK signals were quantified by phosphoimager analysis and normalized to the GAPDH signal and expressed relative to mock control.

FIG. 7 shows the Northern blot analysis of the MyoD-transformed myoblasts treated with oligonucleotide PS58 (20 and 200 nM). The results demonstrate an effective complete inhibition of the disease-causing hDMPK (CUG) 1500 RNA transcript, while the smaller normal hDMPK (CUG)11 RNA transcript is only moderately affected at the two concentrations. Thus, oligonucleotides directed to the repeat region exhibit selectivity towards the larger repeat size (or disease causing expansion).

Example 5 (FIG. 8)

In this example, the DM500 immortomyoblast cell line carrying a human DMPK gene with an approximate (CTG) 500 repeat expansion was cultured, transfected and analysed as described before in example 1. The DM500 myotubes were treated 48 h before harvesting with 200 nM of oligonucleotide PS58, specific to the (CUG) repeat sequence only, oligonucleotide PS113, specific to a sequence in exon 1, or mock control. RT-PCR analysis was performed on hDMPK mRNA expressed in this murine cell line (for primers see example 1) and on three other gene transcripts with a naturally occurring (CUG) repeat in mice, Ptbp1 with a (CUG)6, Syndecan3 with a (CUG)6 and Taxilinbeta with a (CUG)9.

The PCR primers used were for Ptbp1: 5'-TCTGTC-CCTAATGTCCATGG-3' (SEQ ID NO:27) and 5'-GC-CATCTGCACAAGTGCGT-3' (SEQ ID NO:28); for Syndecan3: 5'-GCTGTTGCTGCCACCGCT-3' (SEQ ID NO:29) and 5'-GGCGCCTCGGGAGTGCTA-3' (SEQ ID NO:30); and for Taxilinbeta: 5'-CTCAGCCCTGCTGC-CTGT-3' (SEQ ID NO:31) and 5'-CAGACCCATACGT-GCTTATG-3' (SEQ ID NO:32). The PCR products were run on an agarose gel and signals were quantified using the Labworks 4.0 program (UVP BioImaging systems, Cambridge, United Kingdom). The intensity of each signal was normalized to the corresponding actin signal and expressed relative to mock control.

FIG. 8 shows the RT-PCR results with a maximal inhibition of hDMPK mRNA expression by PS58. The other gene transcripts carrying a naturally occurring small (CUG) repeat were not or only marginally affected by the oligonucleotide PS58, specific to the (CUG) repeat, compared to oligonucleotide PS113, which has no complementary sequence to these gene transcripts.

This example confirms the selectivity of an oligonucleotide, directed solely to the repeat region, towards the long repeat size (or disease causing expansion) compared to naturally occurring shorter repeat sizes.

Example 6 (FIG. 9 en 10)

In this example, the DM500 immortomyoblast cell line carrying a human DMPK gene with an approximate (CTG) 500 repeat expansion was cultured and transfected with PS58 (200 nM). Here, FISH analysis was carried out on the cells. Fourty eight hours after the start of the treatment, the cells were fixed with 4% formaldehyde, 5 mM $MgCl_2$ and 1×PBS for 30 minutes. Hybridization with fluorescently labeled oligonucleotide Cy3-(CAG)10-Cy3 was performed overnight at 37° C. in a humid chamber. After hybridization the material was washed and mounted in mowiol and allowed to dry overnight. Nuclear inclusions (ribonuclear foci) were visualized using a Bio-Rad MRC1024 confocal laser scanning microscope and LaserSharp2000 acquisition software. In total 50 cells were counted and scored for the presence of inclusions in the nuclei of these cells.

Literature indicates that DMPK mRNA containing a (CUG) expanded repeat accumulates and aggregates in the nucleus to form ribonuclear foci with regulatory nuclear proteins and transcription factors. Therefore, normal nuclear gene processing and cell function gets impaired.

FIG. 9 shows a mock treated cell containing ribonuclear inclusions in the nucleus, while these are no longer present in the cell nucleus after treatment with PS58. FIG. 10 shows that the percentage of nuclei containing ribonuclear foci seen under control conditions in DM500 myotubes is strongly decreased by the treatment with PS58. This result demonstrates that inhibition of hDMPK mRNA expression also inhibits the disease related triplet repeat (CUG) rich inclusions.

Example 7 (FIG. 11)

Here, the effect of PS58 was evaluated in vivo in DM500 mice containing hDMPK with a (CTG)n expansion of approximately 500 triplets. The DM500 mice were derived by somatic expansion from the DM300 mouse (e.g. see Gomes-Pereira M et al (2007) PLoS Genet. 2007 3(4): e52). A (CTG) triplet repeat expansion of approximately 500 was confirmed by southern blot and PCR analysis.

In short, PS58 was mixed with transfection agent ExGen 500 (Fermentas) according to the accompanying instructions for in vivo use. PS58 (2 nmol, in the transfection solution with Exgen 500) was injected (40µl) in the GPS complex of one-year-old DM500 mice and this procedure was repeated after 24 h. As a control, DM500 mice were treated similarly with the transfection solution without PS58. After 15 days, the mice were sacrificed, muscles were isolated and total RNA was isolated from the tissues (using Trizol, Invitrogen). RT-PCR analysis was performed to detect hDMPK mRNA in the muscle similar as described above. The intensity of each band was performed using the Labworks 4.0 program (UVP Biolmaging systems, Cambridge, United Kingdom) and normalized to the intensity of the corresponding actin band. Primer location is indicated in the figure.

FIG. 11 shows that in vivo treatment of DM500 mice with PS58 strongly reduced the presence of hDMPK mRNA containing a (CUG)n repeat expansion compared to mock treatment in the *M. plantaris* and *M. gastrocnemius*.

Example 8 (FIG. 12)

In this example, different oligonucleotides (in length and backbone chemistry) but all with a sequence directed solely to the (CTG)n repeat expansion were compared. DM500 myotubes were cultured, transfected and analysed as described above in example 1. Northern blots were quantified by phosphoimager analysis and DMPK signals were normalized to GAPDH.

Here, the DM500 myotubes were treated with the following oligonucleotides (200 nM), all with a complete phosphorothioate backbone (see Table 3).

FIG. 12 shows that treatment of the DM500 myotubes results in a complete reduction of (CUG)n expanded hDMPK mRNA for all oligonucleotides tested. Under the present conditions, the maximal effect obtainable is independent of oligonucleotide length, backbone modification or potential mechanism of inhibition by the employed single stranded oligonucleotides.

Example 9

Fibroblasts (GM 00305) from a male patient with Huntington's Disease were obtained from Coriell Cell Repository (Camden, N.J., US) and cultured according to the accompanying instructions and standard techniques known to the skilled person in the art. Huntington patients carry one healthy and one disease-causing allele of the Huntington gene resulting in the expression of both mRNAs with respectively a normal number and an expanded number of (CAG) repeats, respectively.

The fibroblasts were transfected with a 21-mer 2'O-methyl phosphorothioate RNA antisense oligonucleotide PS57 with a (CUG)7 sequence (SEQ ID NO:5), complementary to the (CAG) triplet repeat in Huntington mRNA. Transfection occurred at 100 or 200 nM in the presence of PEI as indicated by the manufacturer. Twenty four hours after transfection the cells were harvested and total RNA was isolated and analysed by RT-PCR. The Huntington transcript was determined using primers in downstream exon 64 (5' GAAAG TCAGT CCGGG TAGAA CTTC 3' (SEQ ID NO:33) and 5' CAGAT ACCCG CTCCA TAGCA A 3' (SEQ ID NO:34)).

This method detects both types of Huntington mRNAs, the normal and mutant transcript with the additional (CAG) expansion. GAPDH mRNA (housekeeping gene) was also determined. The signals were quantified and the total amount of Huntington mRNA was normalised to the amount of GAPDH mRNA in the same sample. The results are expressed relative to a control treated (without oligonucleotide) sample from fibroblasts (which was to 100%).

In the samples from fibroblasts transfected with either 100 or 200 nM of PS57, significantly lower levels of total Huntington mRNA levels were observed of approximately 53% and 66% compared to the levels in control-treated cells, respectively.

Thus, PS57, an oligonucleotide directed only to the (CAG) repeat, induces a decrease in Huntington mRNA levels and these results are consistent with a selective inhibition of mutant over normal Huntington mRNA.

TABLE 1

Overview oligonucleotides tested

| Oligo name | Modification | Sequence | Position |
|---|---|---|---|
| PS40 | 2'OMe RNA phosphorothioate/ FAM | GAGGGGCGUCCAGG GAUCCG (SEQ ID NO: 1) | intron 14- exon 15 |

TABLE 1 -continued

Overview oligonucleotides tested

| Oligo name | Modification | Sequence | Position |
|---|---|---|---|
| PS41 | 2'OMe RNA phosphorothioate | GCGUCCAGGGAUCC GGACCG (SEQ ID NO: 2) | intron 14-exon 15 |
| PS42 | 2'OMe RNA phosphorothioate | CAGGGAUCCGGACC GGAUAG (SEQ ID NO: 3) | intron 14-exon 15 |
| PS56 | DNA | CAGCAGCAGCAGCA GCAGCAG (SEQ ID NO: 4) | repeat in exon 15 |
| PS58 | 2'OMe RNA phosphorothioate/ FAM | CAGCAGCAGCAGCA GCAGCAG (SEQ ID NO: 6) | repeat in exon 15 |
| P559 | 2'OMe RNA phosphorothioate | UGAGUUGGCCGGCG UGGGCC (SEQ ID NO: 7) | ESE exon 15 |
| PS60 | 2'OMe RNA phosphorothioate | UUCUAGGGUUCAGG GAGCGCGG (SEQ ID NO: 8) | ESE exon 15 |
| PS61 | 2'OMe RNA phosphorothioate | ACUGGAGCUGGGCG GAGACCC (SEQ ID NO: 9) | ESE exon 15 |
| PS62 | 2'OMe RNA phosphorothioate | CUCCCCGGCCGCUA GGGGGC (SEQ ID NO: 10) | ESE exon 15 |
| PS113 | DNA phosphothioroate | GAGCCGCCTCAGCC GCACCTC (SEQ ID NO: 11) | Exon 1 |
| PS114 | DNA phosphothioroate | GAAGTCGGCCACGT ACTTGTC (SEQ ID NO: 12) | Exon 1 |
| PS115 | DNA phosphothioroate | GGAGTCGAAGACAG TTCTAGG (SEQ ID NO: 13) | Exon 15 |
| PS116 | DNA phosphothioroate | GGTACACAGGACTG GAGCTGG (SEQ ID NO: 14) | Exon 15 |

TABLE 2

Reduction of hDMPK mRNA after oligo transfection:

| Oligo | Reduction hDMPK mRNA | SEQ ID No.'s |
|---|---|---|
| PS40 | + | 1 |
| PS41 | − | 2 |
| PS42 | − | 3 |
| PS59 | − | 7 |
| PS60 | − | 8 |
| PS61 | +/− | 9 |
| PS62 | − | 10 |
| PS58 | ++++ | 6 |
| PS56 | − | 4 |
| PS113 | − | 11 |
| PS114 | − | 12 |
| PS115 | +/− | 13 |
| PS116 | + | 14 |

(−) indicates no reduction, (+) indicates level of reduction in hDMPK mRNA.

TABLE 3

Oligonucleotides used in example 9

| # | Length | (CAG)n | Substitution ribose | RNAse H breakdown possible |
|---|---|---|---|---|
| PS58 (SEQ ID NO: 6) | 21-mer | n = 7 | 2'O-Methyl | No |
| PS146 (SEQ ID NO: 16) | 30-mer | n = 10 | 2'O-Methyl | No |
| PS147 (SEQ ID NO: 17) | 15-mer | n = 5 | 2'O-Methyl | No |
| PS142 (SEQ ID NO: 15) | 21-mer | n = 7 | Deoxyribose (DNA) | Yes |

* all oligonucleotides full length phosphorothioate and substitution

---

The invention claimed is:

1. A method for treating myotonic dystrophy type 1 in a subject, comprising administering to the subject an oligonucleotide comprising 10 to 50 nucleotides that is complementary to a repetitive nucleotide unit sequence of a pre-mRNA transcript, wherein the repetitive nucleotide unit is a CUG repetitive nucleotide unit.

2. The method according to claim 1, wherein said repeats are present in a coding sequence of the gene transcript.

3. The method according to claim 1, wherein said repeats are present in a non-coding sequence of the gene transcript.

4. The method according to claim 1, wherein the oligonucleotide comprises a ribonucleotide and/or a deoxyribonucleotide.

5. The method according to claim 4, wherein the oligonucleotide comprises a 2'-O-substituted phosphorothioate nucleotide.

6. The method of claim 5, wherein said oligonucleotide comprises a 2'-O-methyl phosphorothioate nucleotide or a 2'-O-meth[y]oxy ethyl phosphorothioate nucleotide.

7. The method according to claim 1, wherein the oligonucleotide is administered in a nucleic acid vector.

8. The method according to claim 1, wherein the oligonucleotide is in a pharmaceutical composition comprising an excipient and/or a targeting ligand.

9. A method for reducing the number of repeat-containing gene transcripts in a cell comprising providing to said cell an oligonucleotide comprising 10 to 50 nucleotides that is complementary to a repetitive nucleotide unit of a pre-mRNA transcript, wherein said repetitive nucleotide unit is a CUG repetitive nucleotide unit; and wherein the oligonucleotide has a phosphorothioate-containing backbone.

10. The method according to claim 1, wherein the oligonucleotide has a length selected from the group consisting of about 12 to about 30 nucleotides, about 12 to about 45 nucleotides and about 12 to about 25 nucleotides.

11. The method of claim 1, wherein the oligonucleotide has a phosphorothioate-containing backbone.

12. The method according to claim 1, where the oligonucleotide comprises a morpholino phosphorodiamidate oligonucleotide, a phosphorothioate oligonucleotide, a locked nucleic acid (LNA), a peptide nucleic acid (PNA) and/or an ethylene-bridged nucleic acid.

13. The method of claim 1, wherein the oligonucleotide binds only to the sequence of consecutive trinucleotide repeats.

14. The method of claim 1, wherein the oligonucleotide reduces the amount of an aberrant protein.

15. The method of claim 12, wherein the oligonucleotide is a 2'-O-methyl phosphorothioate.

16. The method of claim 15, wherein the oligonucleotide comprises the base sequence of: SEQ ID NO: 6.

* * * * *

SEQUENCE LISTING

<160> NUMBER OF SEQ ID NOS: 36

<210> SEQ ID NO 1
<211> LENGTH: 20
<212> TYPE: RNA
<213> ORGANISM: Unknown
<220> FEATURE:
<223> OTHER INFORMATION: chemically synthesized oligonucleotide PS40

<400> SEQUENCE: 1 gagggcguc cagggauccg                    20

<210> SEQ ID NO 2
<211> LENGTH: 20
<212> TYPE: RNA
<213> ORGANISM: Unknown
<220> FEATURE:
<223> OTHER INFORMATION: chemically synthesized oligonucleotide PS41

```
<400> SEQUENCE: 2
gcguccaggg auccggaccg                                               20

<210> SEQ ID NO 3
<211> LENGTH: 20
<212> TYPE: RNA
<213> ORGANISM: Unknown
<220> FEATURE:
<223> OTHER INFORMATION: chemically synthesized oligonucleotide PS42

<400> SEQUENCE: 3
cagggauccg gaccggauag                                               20

<210> SEQ ID NO 4
<211> LENGTH: 21
<212> TYPE: DNA
<213> ORGANISM: Unknown
<220> FEATURE:
<223> OTHER INFORMATION: chemically synthesized oligonucleotide PS56

<400> SEQUENCE: 4
cagcagcagc agcagcagca g                                             21

<210> SEQ ID NO 5
<211> LENGTH: 21
<212> TYPE: RNA
<213> ORGANISM: Unknown
<220> FEATURE:
<223> OTHER INFORMATION: chemically synthesized oligonucleotide PS57

<400> SEQUENCE: 5
cugcugcugc ugcugcugcu g                                             21

<210> SEQ ID NO 6
<211> LENGTH: 21
<212> TYPE: RNA
<213> ORGANISM: Unknown
<220> FEATURE:
<223> OTHER INFORMATION: chemically synthesized oligonucleotide PS58

<400> SEQUENCE: 6
cagcagcagc agcagcagca g                                             21

<210> SEQ ID NO 7
<211> LENGTH: 20
<212> TYPE: RNA
<213> ORGANISM: Unknown
<220> FEATURE:
<223> OTHER INFORMATION: chemically synthesized oligonucleotide PS59

<400> SEQUENCE: 7
ugaguuggcc ggcgugggcc                                               20

<210> SEQ ID NO 8
<211> LENGTH: 22
<212> TYPE: RNA
<213> ORGANISM: Unknown
<220> FEATURE:
<223> OTHER INFORMATION: chemically synthesized oligonucleotide PS60

<400> SEQUENCE: 8
uucuaggguu cagggagcgc gg                                            22

<210> SEQ ID NO 9
```

```
<211> LENGTH: 21
<212> TYPE: RNA
<213> ORGANISM: Unknown
<220> FEATURE:
<223> OTHER INFORMATION: chemically synthesized oligonucleotide PS61

<400> SEQUENCE: 9
acuggagcug ggcggagacc c                                              21

<210> SEQ ID NO 10
<211> LENGTH: 20
<212> TYPE: RNA
<213> ORGANISM: Unknown
<220> FEATURE:
<223> OTHER INFORMATION: chemically synthesized oligonucleotide PS62

<400> SEQUENCE: 10
cuccccggcc gcuagggggc                                                20

<210> SEQ ID NO 11
<211> LENGTH: 21
<212> TYPE: DNA
<213> ORGANISM: Unknown
<220> FEATURE:
<223> OTHER INFORMATION: chemically synthesized oligonucleotide PS113

<400> SEQUENCE: 11
gagccgcctc agccgcacct c                                              21

<210> SEQ ID NO 12
<211> LENGTH: 21
<212> TYPE: DNA
<213> ORGANISM: Unknown
<220> FEATURE:
<223> OTHER INFORMATION: chemically synthesized oligonucleotide PS114

<400> SEQUENCE: 12
gaagtcggcc acgtacttgt c                                              21

<210> SEQ ID NO 13
<211> LENGTH: 21
<212> TYPE: DNA
<213> ORGANISM: Unknown
<220> FEATURE:
<223> OTHER INFORMATION: chemically synthesized oligonucleotide PS115

<400> SEQUENCE: 13
ggagtcgaag acagttctag g                                              21

<210> SEQ ID NO 14
<211> LENGTH: 21
<212> TYPE: DNA
<213> ORGANISM: Unknown
<220> FEATURE:
<223> OTHER INFORMATION: chemically synthesized oligonucleotide PS116

<400> SEQUENCE: 14
ggtacacagg actggagctg g                                              21

<210> SEQ ID NO 15
<211> LENGTH: 21
<212> TYPE: DNA
<213> ORGANISM: Unknown
<220> FEATURE:
<223> OTHER INFORMATION: chemically synthesized oligonucleotide PS142

<400> SEQUENCE: 15
```

```
cagcagcagc agcagcagca g                                              21

<210> SEQ ID NO 16
<211> LENGTH: 30
<212> TYPE: RNA
<213> ORGANISM: Unknown
<220> FEATURE:
<223> OTHER INFORMATION: chemically synthesized oligonucleotide PS146

<400> SEQUENCE: 16
cagcagcagc agcagcagca gcagcagcag                                     30

<210> SEQ ID NO 17
<211> LENGTH: 15
<212> TYPE: RNA
<213> ORGANISM: Unknown
<220> FEATURE:
<223> OTHER INFORMATION: chemically synthesized oligonucleotide PS147

<400> SEQUENCE: 17
cagcagcagc agcag                                                     15

<210> SEQ ID NO 18
<211> LENGTH: 12
<212> TYPE: RNA
<213> ORGANISM: Unknown
<220> FEATURE:
<223> OTHER INFORMATION: chemically synthesized oligonucleotide (CAG)n

<400> SEQUENCE: 18
cagcagcagc ag                                                        12

<210> SEQ ID NO 19
<211> LENGTH: 12
<212> TYPE: RNA
<213> ORGANISM: Unknown
<220> FEATURE:
<223> OTHER INFORMATION: chemically synthesized oligonucleotide (GCG)n

<400> SEQUENCE: 19
gcggcggcgg cg                                                        12

<210> SEQ ID NO 20
<211> LENGTH: 12
<212> TYPE: RNA
<213> ORGANISM: Unknown
<220> FEATURE:
<223> OTHER INFORMATION: chemically synthesized oligonucleotide (CUG)n

<400> SEQUENCE: 20
cugcugcugc ug                                                        12

<210> SEQ ID NO 21
<211> LENGTH: 12
<212> TYPE: RNA
<213> ORGANISM: Unknown
<220> FEATURE:
<223> OTHER INFORMATION: chemically synthesized oligonucleotide (CGG)n

<400> SEQUENCE: 21
cggcggcggc gg                                                        12

<210> SEQ ID NO 22
<211> LENGTH: 12
<212> TYPE: RNA
```

```
<213> ORGANISM: Unknown
<220> FEATURE:
<223> OTHER INFORMATION: chemically synthesized oligonucleotide (CCUG)n

<400> SEQUENCE: 22
ccugccugcc ug                                                          12

<210> SEQ ID NO 23
<211> LENGTH: 18
<212> TYPE: DNA
<213> ORGANISM: Artificial
<220> FEATURE:
<223> OTHER INFORMATION: primer 1 hDMPK

<400> SEQUENCE: 23
gggggatcac agaccatt                                                    18

<210> SEQ ID NO 24
<211> LENGTH: 21
<212> TYPE: DNA
<213> ORGANISM: Artificial
<220> FEATURE:
<223> OTHER INFORMATION: primer 2 hDMPK

<400> SEQUENCE: 24
tcaatgcatc caaaacgtgg a                                                21

<210> SEQ ID NO 25
<211> LENGTH: 19
<212> TYPE: DNA
<213> ORGANISM: Artificial
<220> FEATURE:
<223> OTHER INFORMATION: Actin sense primer

<400> SEQUENCE: 25
gctaygagct gcctgacgg                                                   19

<210> SEQ ID NO 26
<211> LENGTH: 17
<212> TYPE: DNA
<213> ORGANISM: Artificial
<220> FEATURE:
<223> OTHER INFORMATION: actin antisense primer

<400> SEQUENCE: 26
gaggccagga tggagcc                                                     17

<210> SEQ ID NO 27
<211> LENGTH: 20
<212> TYPE: DNA
<213> ORGANISM: Artificial
<220> FEATURE:
<223> OTHER INFORMATION: primer 1 Ptbp1

<400> SEQUENCE: 27
tctgtcccta atgtccatgg                                                  20

<210> SEQ ID NO 28
<211> LENGTH: 19
<212> TYPE: DNA
<213> ORGANISM: Artificial
<220> FEATURE:
<223> OTHER INFORMATION: primer 2 Ptbp1

<400> SEQUENCE: 28
gccatctgca caagtgcgt                                                   19
```

<210> SEQ ID NO 29
<211> LENGTH: 18
<212> TYPE: DNA
<213> ORGANISM: Artificial
<220> FEATURE:
<223> OTHER INFORMATION: primer 1 Syndecan3

<400> SEQUENCE: 29
gctgttgctg ccaccgct                                       18

<210> SEQ ID NO 30
<211> LENGTH: 18
<212> TYPE: DNA
<213> ORGANISM: Artificial
<220> FEATURE:
<223> OTHER INFORMATION: primer 2 Syndecan3

<400> SEQUENCE: 30
ggcgcctcgg gagtgcta                                       18

<210> SEQ ID NO 31
<211> LENGTH: 18
<212> TYPE: DNA
<213> ORGANISM: Artificial
<220> FEATURE:
<223> OTHER INFORMATION: primer 1 Taxilinbeta

<400> SEQUENCE: 31
ctcagccctg ctgcctgt                                       18

<210> SEQ ID NO 32
<211> LENGTH: 20
<212> TYPE: DNA
<213> ORGANISM: Artificial
<220> FEATURE:
<223> OTHER INFORMATION: primer 2 Taxilinbeta

<400> SEQUENCE: 32
cagacccata cgtgcttatg                                     20

<210> SEQ ID NO 33
<211> LENGTH: 24
<212> TYPE: DNA
<213> ORGANISM: Artificial
<220> FEATURE:
<223> OTHER INFORMATION: primer 1 Huntington

<400> SEQUENCE: 33
gaaagtcagt ccgggtagaa cttc                                24

<210> SEQ ID NO 34
<211> LENGTH: 21
<212> TYPE: DNA
<213> ORGANISM: Artificial
<220> FEATURE:
<223> OTHER INFORMATION: primer 2 Huntington

<400> SEQUENCE: 34
cagatacccg ctccatagca a                                   21

<210> SEQ ID NO 35
<211> LENGTH: 12
<212> TYPE: DNA
<213> ORGANISM: Unknown
<220> FEATURE:

-continued

```
<223> OTHER INFORMATION: chemically synthesized oligonucleotide (GAA)n

<400> SEQUENCE: 35
gaagaagaag aa                                                          12

<210> SEQ ID NO 36
<211> LENGTH: 12
<212> TYPE: DNA
<213> ORGANISM: Unknown
<220> FEATURE:
<223> OTHER INFORMATION: chemically synthesized oligonucleotide (GCC)n

<400> SEQUENCE: 36
gccgccgccg cc                                                          12
```